(12) United States Patent
Stulen et al.

(10) Patent No.: US 9,414,853 B2
(45) Date of Patent: Aug. 16, 2016

(54) ULTRASONIC END EFFECTORS WITH INCREASED ACTIVE LENGTH

(71) Applicant: Ethicon Endo-Surgery, Inc., Cincinnati, OH (US)

(72) Inventors: Foster B. Stulen, Mason, OH (US); Kevin L. Houser, Springboro, OH (US); Vincent P. Battaglia, Jr., Lebanon, OH (US); Brian D. Bertke, Ft. Thomas, KY (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 559 days.

(21) Appl. No.: 13/849,627

(22) Filed: Mar. 25, 2013

(65) Prior Publication Data

US 2013/0226207 A1    Aug. 29, 2013

Related U.S. Application Data

(62) Division of application No. 11/881,662, filed on Jul. 27, 2007, now Pat. No. 8,523,889.

(51) Int. Cl.
*A61B 17/32* (2006.01)

(52) U.S. Cl.
CPC . *A61B 17/320068* (2013.01); *A61B 17/320092* (2013.01); *A61B 2017/320072* (2013.01); *A61B 2017/320076* (2013.01); *A61B 2017/320088* (2013.01)

(58) Field of Classification Search
CPC ............... A61B 17/320068; A61B 17/320092; A61B 2017/320088; A61B 2017/320072; A61B 2017/320076
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |
| 1,813,902 | A | 7/1931 | Bovie |

(Continued)

FOREIGN PATENT DOCUMENTS

| | | |
|---|---|---|
| AU | 2003241752 A1 | 9/2003 |
| CA | 2535467 A1 | 4/1993 |

(Continued)

OTHER PUBLICATIONS

International Search Report for PCT/US2008/070997, Jan. 5, 2009 (5 pages).

(Continued)

*Primary Examiner* — Ashley Fishback

(57) ABSTRACT

A surgical instrument includes an end effector having a proximal end segment, a distal end segment, and an insert segment. The proximal end segment and the distal end segment are composed of a first material. The insert segment is composed of a second material. The insert segment is located between the proximal end segment and the distal end segment along the longitudinal axis of the end effector. The insert segment functions to bridge or fill the nodal energy gap. A surgical instrument includes a transducer configured to produce vibrations along a longitudinal axis as a predetermined frequency. An ultrasonic blade extends along the longitudinal axis coupled to the transducer. An insert segment or a pad is positioned adjacent to the blade such that it engages the blade when the surgical instrument is in a closed position and generates heat filling the nodal energy gap.

15 Claims, 21 Drawing Sheets

(56) References Cited

U.S. PATENT DOCUMENTS

| | | |
|---|---|---|
| 2,188,497 A | 1/1940 | Calva |
| 2,442,966 A | 6/1948 | Wallace |
| 2,597,564 A | 5/1952 | Bugg |
| 2,704,333 A | 3/1955 | Calosi et al. |
| 2,736,960 A | 3/1956 | Armstrong |
| 2,845,072 A | 7/1958 | Shafer |
| 2,849,788 A | 9/1958 | Creek |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,526,219 A | 9/1970 | Balamuth |
| 3,554,198 A | 1/1971 | Tatoian et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,776,238 A | 12/1973 | Peyman et al. |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 4,012,647 A | 3/1977 | Balamuth et al. |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,444 A | 5/1980 | Bonnell et al. |
| 4,300,083 A | 11/1981 | Heiges |
| 4,302,728 A | 11/1981 | Nakamura |
| 4,306,570 A | 12/1981 | Matthews |
| 4,445,063 A | 4/1984 | Smith |
| 4,491,132 A | 1/1985 | Aikins |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,545,374 A | 10/1985 | Jacobson |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,708,127 A | 11/1987 | Abdelghani |
| 4,712,722 A | 12/1987 | Hood et al. |
| 4,808,154 A | 2/1989 | Freeman |
| 4,819,635 A | 4/1989 | Shapiro |
| 4,827,911 A | 5/1989 | Broadwin et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,850,354 A | 7/1989 | McGurk-Burleson et al. |
| 4,852,578 A | 8/1989 | Companion et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,881,550 A | 11/1989 | Kothe |
| 4,896,009 A | 1/1990 | Pawlowski |
| 4,903,696 A | 2/1990 | Stasz et al. |
| 4,915,643 A | 4/1990 | Samejima et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,013,956 A | 5/1991 | Kurozumi et al. |
| 5,015,227 A | 5/1991 | Broadwin et al. |
| 5,026,370 A | 6/1991 | Lottick |
| 5,026,387 A | 6/1991 | Thomas |
| 5,042,707 A | 8/1991 | Taheri |
| 5,084,052 A | 1/1992 | Jacobs |
| 5,105,117 A | 4/1992 | Yamaguchi |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,162,044 A | 11/1992 | Gahn et al. |
| 5,163,421 A | 11/1992 | Bernstein et al. |
| 5,163,537 A | 11/1992 | Radev |
| 5,167,725 A | 12/1992 | Clark et al. |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,209,719 A | 5/1993 | Baruch et al. |
| 5,213,569 A | 5/1993 | Davis |
| 5,214,339 A | 5/1993 | Naito |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,261,922 A | 11/1993 | Hood |
| 5,263,957 A | 11/1993 | Davison |
| 5,264,925 A | 11/1993 | Shipp et al. |
| 5,275,166 A | 1/1994 | Vaitekunas et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,312,023 A | 5/1994 | Green et al. |
| 5,312,425 A | 5/1994 | Evans et al. |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |

(56) References Cited

U.S. PATENT DOCUMENTS

| | | |
|---|---|---|
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,387,215 A | 2/1995 | Fisher |
| 5,389,098 A | 2/1995 | Tsuruta et al. |
| 5,394,187 A | 2/1995 | Shipp |
| 5,396,266 A | 3/1995 | Brimhall |
| 5,403,312 A | 4/1995 | Yates et al. |
| 5,403,334 A | 4/1995 | Evans et al. |
| 5,408,268 A | 4/1995 | Shipp |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,423,844 A | 6/1995 | Miller |
| 5,438,997 A | 8/1995 | Sieben et al. |
| 5,445,639 A | 8/1995 | Kuslich et al. |
| 5,449,370 A | 9/1995 | Vaitekunas |
| 5,451,220 A | 9/1995 | Ciervo |
| 5,456,684 A | 10/1995 | Schmidt et al. |
| 5,471,988 A | 12/1995 | Fujio et al. |
| 5,472,443 A | 12/1995 | Cordis et al. |
| 5,478,003 A | 12/1995 | Green et al. |
| 5,483,501 A | 1/1996 | Park et al. |
| 5,486,162 A | 1/1996 | Brumbach |
| 5,490,860 A | 2/1996 | Middle et al. |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,540,693 A | 7/1996 | Fisher |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,573,424 A | 11/1996 | Poppe |
| 5,577,654 A | 11/1996 | Bishop |
| 5,591,187 A | 1/1997 | Dekel |
| 5,593,414 A | 1/1997 | Shipp et al. |
| 5,601,601 A | 2/1997 | Tal et al. |
| 5,603,773 A | 2/1997 | Campbell |
| 5,607,436 A | 3/1997 | Pratt et al. |
| 5,618,304 A | 4/1997 | Hart et al. |
| 5,618,492 A | 4/1997 | Auten et al. |
| 5,620,447 A | 4/1997 | Smith et al. |
| 5,626,587 A | 5/1997 | Bishop et al. |
| 5,626,595 A | 5/1997 | Sklar et al. |
| 5,628,760 A | 5/1997 | Knoepfler |
| 5,630,420 A | 5/1997 | Vaitekunas |
| 5,632,717 A | 5/1997 | Yoon |
| 5,640,741 A | 6/1997 | Yano |
| D381,077 S | 7/1997 | Hunt |
| 5,651,780 A | 7/1997 | Jackson et al. |
| 5,653,713 A | 8/1997 | Michelson |
| 5,662,662 A | 9/1997 | Bishop et al. |
| 5,669,922 A | 9/1997 | Hood |
| 5,674,235 A | 10/1997 | Parisi |
| 5,678,568 A | 10/1997 | Uchikubo et al. |
| 5,690,269 A | 11/1997 | Bolanos et al. |
| 5,694,936 A | 12/1997 | Fujimoto et al. |
| 5,700,261 A | 12/1997 | Brinkerhoff |
| 5,704,534 A | 1/1998 | Huitema et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,717,306 A | 2/1998 | Shipp |
| 5,728,130 A | 3/1998 | Ishikawa et al. |
| 5,730,752 A | 3/1998 | Alden et al. |
| 5,733,074 A | 3/1998 | Stöck et al. |
| 5,741,226 A | 4/1998 | Strukel et al. |
| 5,766,164 A | 6/1998 | Mueller et al. |
| 5,772,659 A | 6/1998 | Becker et al. |
| 5,792,135 A | 8/1998 | Madhani et al. |
| 5,792,138 A | 8/1998 | Shipp |
| 5,792,165 A | 8/1998 | Klieman et al. |
| 5,797,959 A | 8/1998 | Castro et al. |
| 5,805,140 A | 9/1998 | Rosenberg et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,957 A | 11/1998 | Schulz et al. |
| 5,843,109 A | 12/1998 | Mehta et al. |
| 5,851,212 A | 12/1998 | Zirps et al. |
| 5,858,018 A | 1/1999 | Shipp et al. |
| 5,873,873 A | 2/1999 | Smith et al. |
| 5,873,882 A | 2/1999 | Straub et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,627 A | 5/1999 | Spaulding |
| 5,906,628 A | 5/1999 | Miyawaki et al. |
| 5,911,699 A | 6/1999 | Anis et al. |
| 5,916,229 A | 6/1999 | Evans |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,024,741 A | 2/2000 | Williamson, IV et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,048,224 A | 4/2000 | Kay |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |

(56) References Cited

U.S. PATENT DOCUMENTS

| | | |
|---|---|---|
| 6,096,033 A | 8/2000 | Tu et al. |
| 6,099,542 A | 8/2000 | Cohn et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,147,560 A | 11/2000 | Erhage et al. |
| 6,152,902 A | 11/2000 | Christian et al. |
| 6,154,198 A | 11/2000 | Rosenberg |
| 6,159,160 A | 12/2000 | Hsei et al. |
| 6,159,175 A | 12/2000 | Strukel et al. |
| 6,162,194 A | 12/2000 | Shipp |
| 6,165,150 A | 12/2000 | Banko |
| 6,174,310 B1 | 1/2001 | Kirwan, Jr. |
| 6,179,853 B1 | 1/2001 | Sachse et al. |
| 6,183,426 B1 | 2/2001 | Akisada et al. |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,233,476 B1 | 5/2001 | Strommer et al. |
| 6,238,366 B1 | 5/2001 | Savage et al. |
| 6,245,065 B1 | 6/2001 | Panescu et al. |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,299,591 B1 | 10/2001 | Banko |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,350,269 B1 | 2/2002 | Shipp et al. |
| 6,352,532 B1 | 3/2002 | Kramer et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,109 B1 | 5/2002 | Davison et al. |
| 6,388,657 B1 | 5/2002 | Natoli |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,538 B1 | 8/2002 | Blewett et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,500,312 B2 | 12/2002 | Wedekamp |
| 6,506,208 B2 | 1/2003 | Hunt et al. |
| 6,511,478 B1 | 1/2003 | Burnside et al. |
| 6,511,493 B1 | 1/2003 | Moutafis et al. |
| 6,514,267 B2 | 2/2003 | Jewett |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,558,376 B2 | 5/2003 | Bishop |
| 6,561,983 B2 | 5/2003 | Cronin et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| D477,408 S | 7/2003 | Bromley |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,607,540 B1 | 8/2003 | Shipp |
| 6,610,059 B1 | 8/2003 | West, Jr. |
| 6,616,450 B2 | 9/2003 | Mossle et al. |
| 6,619,529 B2 | 9/2003 | Green et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,644,532 B2 | 11/2003 | Green et al. |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |

(56) References Cited

U.S. PATENT DOCUMENTS

| | | |
|---|---|---|
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,716,215 B1 | 4/2004 | David et al. |
| 6,719,692 B2 | 4/2004 | Kleffner et al. |
| 6,719,776 B2 | 4/2004 | Baxter |
| 6,723,091 B2 | 4/2004 | Goble et al. |
| D490,059 S | 5/2004 | Conway et al. |
| 6,731,047 B2 | 5/2004 | Kauf et al. |
| 6,733,506 B1 | 5/2004 | McDevitt et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,770,072 B1 | 8/2004 | Truckai et al. |
| 6,773,409 B2 | 8/2004 | Truckai et al. |
| 6,773,443 B2 | 8/2004 | Truwit et al. |
| 6,773,444 B2 | 8/2004 | Messerly |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,790,173 B2 | 9/2004 | Saadat et al. |
| 6,790,216 B1 | 9/2004 | Ishikawa |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,827,712 B2 | 12/2004 | Tovey et al. |
| 6,828,712 B2 | 12/2004 | Battaglin et al. |
| 6,835,082 B2 | 12/2004 | Gonnering |
| 6,849,073 B2 | 2/2005 | Hoey et al. |
| 6,860,878 B2 | 3/2005 | Brock |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,899,685 B2 | 5/2005 | Kermode et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,929,602 B2 | 8/2005 | Hirakui et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,994,708 B2 | 2/2006 | Manzo |
| 7,001,335 B2 | 2/2006 | Adachi et al. |
| 7,011,657 B2 | 3/2006 | Truckai et al. |
| 7,014,638 B2 | 3/2006 | Michelson |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,066,893 B2 | 6/2006 | Hibner et al. |
| 7,066,895 B2 | 6/2006 | Podany |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,618 B2 | 8/2006 | Couture |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,207,997 B2 | 4/2007 | Shipp et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,235,071 B2 | 6/2007 | Gonnering |
| 7,244,262 B2 | 7/2007 | Wiener et al. |
| 7,258,688 B1 | 8/2007 | Shah et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupré |
| 7,300,431 B2 | 11/2007 | Dubrovsky |
| 7,300,435 B2 | 11/2007 | Wham et al. |

(56) References Cited

U.S. PATENT DOCUMENTS

| | | |
|---|---|---|
| 7,300,446 B2 | 11/2007 | Beaupre |
| 7,303,531 B2 | 12/2007 | Lee et al. |
| 7,303,557 B2 | 12/2007 | Wham et al. |
| 7,306,597 B2 | 12/2007 | Manzo |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,364,577 B2 | 4/2008 | Wham et al. |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,462,181 B2 | 12/2008 | Kraft et al. |
| 7,464,846 B2 | 12/2008 | Sheltion, IV et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,494,468 B2 | 2/2009 | Rabiner et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,549,564 B2 | 6/2009 | Boudreaux |
| 7,559,450 B2 | 7/2009 | Wales et al. |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,095 B2 | 9/2009 | Shipp et al. |
| 7,585,181 B2 | 9/2009 | Olsen |
| 7,588,176 B2 | 9/2009 | Timm et al. |
| 7,601,119 B2 | 10/2009 | Shahinian |
| 7,607,557 B2 | 10/2009 | Shelton, IV et al. |
| 7,621,930 B2 | 11/2009 | Houser |
| 7,641,653 B2 | 1/2010 | Dalla Betta et al. |
| 7,654,431 B2 | 2/2010 | Hueil et al. |
| 7,659,833 B2 | 2/2010 | Warner et al. |
| 7,665,647 B2 | 2/2010 | Shelton, IV et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,846 B2 | 4/2010 | Ryan |
| 7,713,202 B2 | 5/2010 | Boukhny et al. |
| 7,714,481 B2 | 5/2010 | Sakai |
| 7,717,312 B2 | 5/2010 | Beetel |
| 7,717,915 B2 | 5/2010 | Miyazawa |
| D618,797 S | 6/2010 | Price et al. |
| 7,726,537 B2 | 6/2010 | Olson et al. |
| 7,727,177 B2 | 6/2010 | Bayat |
| 7,738,969 B2 | 6/2010 | Bleich |
| 7,740,594 B2 | 6/2010 | Hibner |
| 7,751,115 B2 | 7/2010 | Song |
| D621,503 S | 8/2010 | Otten et al. |
| 7,766,210 B2 | 8/2010 | Shelton, IV et al. |
| 7,766,693 B2 | 8/2010 | Sartor et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,784,662 B2 | 8/2010 | Wales et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,819,819 B2 | 10/2010 | Quick et al. |
| 7,821,143 B2 | 10/2010 | Wiener |
| D627,066 S | 11/2010 | Romero |
| 7,824,401 B2 | 11/2010 | Manzo et al. |
| 7,832,611 B2 | 11/2010 | Boyden et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,892,606 B2 | 2/2011 | Thies et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,824 B2 | 3/2011 | Masuda et al. |
| 7,922,061 B2 | 4/2011 | Shelton, IV et al. |
| 7,922,651 B2 | 4/2011 | Yamada et al. |
| D637,288 S | 5/2011 | Houghton |
| D638,540 S | 5/2011 | Ijiri et al. |
| 7,936,203 B2 | 5/2011 | Zimlich |
| 7,951,095 B2 | 5/2011 | Makin et al. |
| 7,951,165 B2 | 5/2011 | Golden et al. |
| 7,959,050 B2 | 6/2011 | Smith et al. |
| 7,959,626 B2 | 6/2011 | Hong et al. |
| 7,972,329 B2 | 7/2011 | Refior et al. |
| 7,976,544 B2 | 7/2011 | McClurken et al. |
| 7,981,050 B2 | 7/2011 | Ritchart et al. |
| 7,998,157 B2 | 8/2011 | Culp et al. |
| 8,038,693 B2 | 10/2011 | Allen |

(56) References Cited

U.S. PATENT DOCUMENTS

| | | |
|---|---|---|
| 8,057,498 B2 | 11/2011 | Robertson |
| 8,058,771 B2 | 11/2011 | Giordano et al. |
| 8,061,014 B2 | 11/2011 | Smith et al. |
| 8,070,711 B2 | 12/2011 | Bassinger et al. |
| 8,070,762 B2 | 12/2011 | Escudero et al. |
| 8,075,558 B2 | 12/2011 | Truckai et al. |
| 8,089,197 B2 | 1/2012 | Rinner et al. |
| 8,097,012 B2 | 1/2012 | Kagarise |
| 8,105,323 B2 | 1/2012 | Buysse et al. |
| 8,142,461 B2 | 3/2012 | Houser et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,877 B2 | 5/2012 | Klimovitch et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,502 B2 | 6/2012 | Smith et al. |
| 8,207,651 B2 | 6/2012 | Gilbert |
| 8,210,411 B2 | 7/2012 | Yates et al. |
| 8,226,675 B2 | 7/2012 | Houser et al. |
| 8,235,917 B2 | 8/2012 | Joseph et al. |
| 8,236,019 B2 | 8/2012 | Houser |
| 8,236,020 B2 | 8/2012 | Smith et al. |
| 8,241,271 B2 | 8/2012 | Millman et al. |
| 8,246,575 B2 | 8/2012 | Viola |
| 8,246,615 B2 | 8/2012 | Behnke |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,273,087 B2 | 9/2012 | Kimura et al. |
| D669,992 S | 10/2012 | Schafer et al. |
| D669,993 S | 10/2012 | Merchant et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,888 B2 | 10/2012 | Whitman |
| 8,298,223 B2 | 10/2012 | Wham et al. |
| 8,298,225 B2 | 10/2012 | Gilbert |
| 8,303,576 B2 | 11/2012 | Brock |
| 8,303,580 B2 | 11/2012 | Wham et al. |
| 8,303,583 B2 | 11/2012 | Hosier et al. |
| 8,319,400 B2 | 11/2012 | Houser et al. |
| 8,323,302 B2 | 12/2012 | Robertson et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,344,596 B2 | 1/2013 | Nield et al. |
| 8,348,967 B2 | 1/2013 | Stulen |
| 8,357,103 B2 | 1/2013 | Mark et al. |
| 8,366,727 B2 | 2/2013 | Witt et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,545 B2 | 4/2013 | Smith et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,664 B2 | 5/2013 | Balanev et al. |
| 8,460,288 B2 | 6/2013 | Tamai et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,485,413 B2 | 7/2013 | Scheib et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,359 B2 | 8/2013 | Whitman et al. |
| 8,512,365 B2 | 8/2013 | Wiener et al. |
| 8,531,064 B2 | 9/2013 | Robertson et al. |
| 8,535,340 B2 | 9/2013 | Allen |
| 8,535,341 B2 | 9/2013 | Allen |
| 8,546,996 B2 | 10/2013 | Messerly et al. |
| 8,546,999 B2 | 10/2013 | Houser et al. |
| 8,568,400 B2 | 10/2013 | Gilbert |
| 8,573,461 B2 | 11/2013 | Shelton, IV et al. |
| 8,573,465 B2 | 11/2013 | Shelton, IV |
| 8,579,928 B2 | 11/2013 | Robertson et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,616,431 B2 | 12/2013 | Timm et al. |
| 8,623,027 B2 | 1/2014 | Price et al. |
| 8,650,728 B2 | 2/2014 | Wan et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,690,582 B2 | 4/2014 | Rohrbach et al. |
| 8,696,366 B2 | 4/2014 | Chen et al. |
| 8,704,425 B2 | 4/2014 | Giordano et al. |
| 8,709,031 B2 | 4/2014 | Stulen |
| 8,749,116 B2 | 6/2014 | Messerly et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,764,735 B2 | 7/2014 | Coe et al. |
| 8,773,001 B2 | 7/2014 | Wiener et al. |
| 8,779,648 B2 | 7/2014 | Giordano et al. |
| 8,784,418 B2 | 7/2014 | Romero |
| 8,808,319 B2 | 8/2014 | Houser et al. |
| 8,827,992 B2 | 9/2014 | Koss et al. |
| 8,845,537 B2 | 9/2014 | Tanaka et al. |
| 8,882,791 B2 | 11/2014 | Stulen |
| 8,888,776 B2 | 11/2014 | Dietz et al. |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,911,460 B2 | 12/2014 | Neurohr et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,547 B2 | 2/2015 | Dietz et al. |
| 8,968,355 B2 | 3/2015 | Malkowski et al. |
| 8,974,477 B2 | 3/2015 | Yamada |
| 8,979,890 B2 | 3/2015 | Boudreaux |

(56) References Cited

U.S. PATENT DOCUMENTS

| | | |
|---|---|---|
| 8,986,287 B2 | 3/2015 | Park et al. |
| 8,986,302 B2 | 3/2015 | Aldridge et al. |
| 8,989,903 B2 | 3/2015 | Weir et al. |
| 9,017,326 B2 | 4/2015 | DiNardo et al. |
| 9,039,695 B2 | 5/2015 | Giordano et al. |
| 9,044,261 B2 | 6/2015 | Houser |
| 9,050,093 B2 | 6/2015 | Aldridge et al. |
| 9,050,124 B2 | 6/2015 | Houser |
| 9,060,775 B2 | 6/2015 | Wiener et al. |
| 9,060,776 B2 | 6/2015 | Yates et al. |
| 9,066,747 B2 | 6/2015 | Robertson |
| 9,072,539 B2 | 7/2015 | Messerly et al. |
| 9,089,360 B2 | 7/2015 | Messerly et al. |
| 9,095,367 B2 | 8/2015 | Olson et al. |
| 9,107,689 B2 | 8/2015 | Robertson et al. |
| 9,113,940 B2 | 8/2015 | Twomey |
| 9,168,054 B2 | 10/2015 | Turner et al. |
| 9,198,714 B2 | 12/2015 | Worrell et al. |
| 9,220,527 B2 | 12/2015 | Houser et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,921 B2 | 1/2016 | Messerly et al. |
| 9,241,728 B2 | 1/2016 | Price et al. |
| 9,241,731 B2 | 1/2016 | Boudreaux et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0014087 A1 | 1/2003 | Fang et al. |
| 2003/0036705 A1 | 2/2003 | Hare et al. |
| 2003/0050572 A1 | 3/2003 | Brautigam et al. |
| 2003/0055443 A1 | 3/2003 | Spotnitz |
| 2003/0114851 A1 | 6/2003 | Truckai et al. |
| 2003/0144680 A1 | 7/2003 | Kellogg et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0132383 A1 | 7/2004 | Langford et al. |
| 2004/0147934 A1 | 7/2004 | Kiester |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0199193 A1 | 10/2004 | Hayashi et al. |
| 2004/0204728 A1 | 10/2004 | Haefner |
| 2004/0243147 A1 | 12/2004 | Lipow |
| 2004/0260300 A1 | 12/2004 | Gorensek et al. |
| 2005/0021018 A1 | 1/2005 | Anderson et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079878 A1 | 4/2006 | Houser |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0271030 A1 | 11/2006 | Francis et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0074584 A1 | 4/2007 | Talarico et al. |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0191712 A1 | 8/2007 | Messerly et al. |
| 2007/0219481 A1 | 9/2007 | Babaev |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1 | 12/2007 | Lee |
| 2008/0009848 A1 | 1/2008 | Paraschiv et al. |
| 2008/0013809 A1 | 1/2008 | Zhu et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0077145 A1 | 3/2008 | Boyden et al. |

(56) References Cited

U.S. PATENT DOCUMENTS

| | | |
|---|---|---|
| 2008/0082039 A1 | 4/2008 | Babaev |
| 2008/0082098 A1 | 4/2008 | Tanaka et al. |
| 2008/0097501 A1 | 4/2008 | Blier |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2009/0023985 A1 | 1/2009 | Ewers |
| 2009/0030311 A1 | 1/2009 | Stulen et al. |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0088785 A1 | 4/2009 | Masuda |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0207923 A1 | 8/2009 | Dress |
| 2009/0216157 A1 | 8/2009 | Yamada |
| 2009/0223033 A1 | 9/2009 | Houser |
| 2009/0254077 A1 | 10/2009 | Craig |
| 2009/0254080 A1 | 10/2009 | Honda |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270899 A1 | 10/2009 | Carusillo et al. |
| 2009/0275940 A1 | 11/2009 | Malackowski et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0036370 A1 | 2/2010 | Mirel et al. |
| 2010/0042077 A1 | 2/2010 | Okada |
| 2010/0049180 A1 | 2/2010 | Wells et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0222714 A1 | 9/2010 | Muir et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0077648 A1 | 3/2011 | Lee et al. |
| 2011/0087218 A1 | 4/2011 | Boudreaux et al. |
| 2011/0112526 A1 | 5/2011 | Fritz et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0196399 A1 | 8/2011 | Robertson et al. |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0290853 A1 | 12/2011 | Shelton, IV et al. |
| 2011/0290856 A1 | 12/2011 | Shelton, IV et al. |
| 2012/0004655 A1 | 1/2012 | Kim et al. |
| 2012/0022525 A1 | 1/2012 | Dietz et al. |
| 2012/0022530 A1 | 1/2012 | Woodruff et al. |
| 2012/0022583 A1 | 1/2012 | Sugalski et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0101495 A1 | 4/2012 | Young et al. |
| 2012/0101501 A1 | 4/2012 | Nishimura et al. |
| 2012/0109159 A1 | 5/2012 | Jordan et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0136354 A1 | 5/2012 | Rupp |
| 2012/0138660 A1 | 6/2012 | Shelton, IV |
| 2012/0143211 A1 | 6/2012 | Kishi |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199632 A1 | 8/2012 | Spivey et al. |
| 2012/0203143 A1 | 8/2012 | Sanai et al. |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0215220 A1 | 8/2012 | Manzo et al. |
| 2012/0245582 A1 | 9/2012 | Kimball et al. |
| 2012/0253370 A1 | 10/2012 | Ross et al. |
| 2012/0269676 A1 | 10/2012 | Houser et al. |
| 2012/0330307 A1 | 12/2012 | Ladtkow et al. |
| 2013/0012957 A1 | 1/2013 | Shelton, IV et al. |
| 2013/0030433 A1 | 1/2013 | Heard |
| 2013/0035680 A1 | 2/2013 | Ben-Haim et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0165929 A1 | 6/2013 | Muir et al. |
| 2013/0217967 A1 | 8/2013 | Mohr et al. |

(56) References Cited

U.S. PATENT DOCUMENTS

| | | |
|---|---|---|
| 2013/0226208 A1 | 8/2013 | Wiener et al. |
| 2013/0245659 A1 | 9/2013 | Robertson et al. |
| 2013/0253498 A1 | 9/2013 | Germain et al. |
| 2013/0267975 A1 | 10/2013 | Timm et al. |
| 2013/0274734 A1 | 10/2013 | Maass et al. |
| 2013/0282038 A1 | 10/2013 | Dannaher et al. |
| 2013/0282039 A1 | 10/2013 | Wiener et al. |
| 2013/0296908 A1 | 11/2013 | Schulte et al. |
| 2013/0338661 A1 | 12/2013 | Behnke, II |
| 2013/0345689 A1 | 12/2013 | Ruddenklau et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005668 A1 | 1/2014 | Rhee et al. |
| 2014/0005676 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0243864 A1 | 8/2014 | Voegele et al. |
| 2014/0276970 A1 | 9/2014 | Messerly et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0250495 A1 | 9/2015 | Robertson et al. |
| 2015/0257780 A1 | 9/2015 | Houser |
| 2015/0257781 A1 | 9/2015 | Houser et al. |
| 2015/0265308 A1 | 9/2015 | Houser et al. |
| 2015/0282834 A1 | 10/2015 | Robertson |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351789 A1 | 12/2015 | Robertson et al. |
| 2016/0030076 A1 | 2/2016 | Faller et al. |

FOREIGN PATENT DOCUMENTS

| | | | |
|---|---|---|---|
| CN | 1233944 A | 11/1999 | |
| CN | 1253485 A | 5/2000 | |
| CN | 1634601 A | 7/2005 | |
| CN | 1640365 A | 7/2005 | |
| CN | 1694649 A | 11/2005 | |
| CN | 1922563 A | 2/2007 | |
| CN | 1951333 A | 4/2007 | |
| CN | 101040799 A | 9/2007 | |
| CN | 101467917 A | 1/2009 | |
| DE | 3904558 A1 | 8/1990 | |
| DE | 9210327 U1 | 11/1992 | |
| DE | 4323585 A1 | 1/1995 | |
| DE | 19608716 C1 | 4/1997 | |
| DE | 20021619 U1 | 3/2001 | |
| DE | 10042606 A1 | 8/2001 | |
| EP | 0136855 B1 | 9/1984 | |
| EP | 0171967 A2 | 2/1986 | |
| EP | 1839599 A1 | 10/1987 | |
| EP | 0336742 A2 | 4/1989 | |
| EP | 0342448 A1 | 11/1989 | |
| EP | 0424685 B1 | 5/1991 | |
| EP | 0443256 A1 | 8/1991 | |
| EP | 0456470 A1 | 11/1991 | |
| EP | 0598976 A2 | 1/1994 | |
| EP | 0677275 A2 | 3/1995 | |
| EP | 0482195 B1 | 1/1996 | |
| EP | 0695535 A1 | 2/1996 | |
| EP | 0741996 A2 | 11/1996 | |
| EP | 0612570 B1 | 6/1997 | |
| EP | 1108394 A2 | 6/2001 | |
| EP | 1138264 A1 | 10/2001 | |
| EP | 0908148 B1 | 1/2002 | |
| EP | 1229515 A2 | 8/2002 | |
| EP | 1285634 A1 | 2/2003 | |
| EP | 0908155 B1 | 6/2003 | |
| EP | 0705570 B1 | 4/2004 | |
| EP | 0765637 B1 | 7/2004 | |
| EP | 0870473 B1 | 9/2005 | |
| EP | 0624346 B1 | 11/2005 | |
| EP | 1594209 A1 | 11/2005 | |
| EP | 1199044 B1 | 12/2005 | |
| EP | 1609428 A1 | 12/2005 | |
| EP | 1199043 B1 | 3/2006 | |
| EP | 1433425 B1 | 6/2006 | |
| EP | 1256323 B1 | 9/2006 | |
| EP | 1698289 A2 | 9/2006 | |
| EP | 1704824 A1 | 9/2006 | |
| EP | 1749479 A1 | 2/2007 | |
| EP | 1815950 A1 | 8/2007 | |
| EP | 1844720 A1 | 10/2007 | |
| EP | 1862133 A1 | 12/2007 | |
| EP | 1875875 A1 | 1/2008 | |
| EP | 1199045 B1 | 6/2008 | |
| EP | 1964530 A1 | 9/2008 | |
| EP | 1972264 A1 | 9/2008 | |
| EP | 1974771 A1 | 10/2008 | |
| EP | 1435852 B1 | 12/2008 | |
| EP | 1498082 B1 | 12/2008 | |
| EP | 1707131 B1 | 12/2008 | |
| EP | 1997438 A2 | 12/2008 | |
| EP | 1477104 B1 | 1/2009 | |
| EP | 2014218 A2 | 1/2009 | |
| EP | 2042112 A2 | 4/2009 | |
| EP | 1832259 B1 | 6/2009 | |
| EP | 2074959 A1 | 7/2009 | |
| EP | 2106758 A1 | 10/2009 | |
| EP | 2111813 A1 | 10/2009 | |
| EP | 2200145 A1 | 6/2010 | |
| EP | 1214913 B1 | 7/2010 | |
| EP | 2238938 A1 | 10/2010 | |
| EP | 2298154 A2 | 3/2011 | |
| EP | 1510178 B1 | 6/2011 | |
| EP | 2305144 A1 | 6/2011 | |
| EP | 2335630 A1 | 6/2011 | |
| EP | 1502551 B1 | 7/2011 | |
| EP | 2361562 A1 | 8/2011 | |
| EP | 2365608 A2 | 9/2011 | |
| EP | 2420197 A2 | 2/2012 | |
| EP | 2422721 A2 | 2/2012 | |
| EP | 1927321 B1 | 4/2012 | |
| EP | 2510891 A1 | 10/2012 | |
| EP | 2316359 B1 | 3/2013 | |
| EP | 1586275 B1 | 5/2013 | |

(56) References Cited

FOREIGN PATENT DOCUMENTS

| | | |
|---|---|---|
| EP | 1616529 B1 | 9/2013 |
| EP | 2583633 B1 | 10/2014 |
| GB | 1482943 A | 8/1977 |
| GB | 2032221 A | 4/1980 |
| GB | 2317566 A | 4/1998 |
| GB | 2379878 B | 11/2004 |
| GB | 2447767 B | 8/2011 |
| JP | S 50-100891 | 12/1973 |
| JP | S 59-68513 | 10/1982 |
| JP | S 59141938 A | 8/1984 |
| JP | 62-221343 A | 9/1987 |
| JP | S 62-227343 | 10/1987 |
| JP | 62-292153 A | 12/1987 |
| JP | S 62-292154 A | 12/1987 |
| JP | 63-109386 A | 5/1988 |
| JP | 63-315049 A | 12/1988 |
| JP | H 01-151452 A | 6/1989 |
| JP | H 01-198540 A | 8/1989 |
| JP | 02-71510 U | 5/1990 |
| JP | 2-286149 A | 11/1990 |
| JP | H 02-292193 A | 12/1990 |
| JP | H 03-37061 A | 2/1991 |
| JP | 04-25707 U | 2/1992 |
| JP | H 04-64351 A | 2/1992 |
| JP | 4-30508 U | 3/1992 |
| JP | H 04-150847 A | 5/1992 |
| JP | H 04-152942 A | 5/1992 |
| JP | 05-095955 A | 4/1993 |
| JP | H 05-115490 A | 5/1993 |
| JP | H 06-070938 A | 3/1994 |
| JP | 6-104503 A | 4/1994 |
| JP | 6-507081 A | 8/1994 |
| JP | H 06-217988 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 08-299351 A | 11/1996 |
| JP | H 08-336545 A | 12/1996 |
| JP | H 09-503146 A | 3/1997 |
| JP | H 09-135553 A | 5/1997 |
| JP | H 09-140722 A | 6/1997 |
| JP | H 10-005237 A | 1/1998 |
| JP | 10-295700 A | 11/1998 |
| JP | H 11-501543 A | 2/1999 |
| JP | H 11-128238 A | 5/1999 |
| JP | H 11-192235 A | 7/1999 |
| JP | 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-287987 A | 10/2000 |
| JP | 2001-029353 A | 2/2001 |
| JP | 2001-502216 A | 2/2001 |
| JP | 2003612 | 6/2001 |
| JP | 2001-309925 A | 11/2001 |
| JP | 2002-186901 A | 7/2002 |
| JP | 2002-204808 A | 7/2002 |
| JP | 2002-263579 A | 9/2002 |
| JP | 2002-301086 A | 10/2002 |
| JP | 2002-330977 A | 11/2002 |
| JP | 2002-542690 A | 12/2002 |
| JP | 2003-000612 A | 1/2003 |
| JP | 2003-010201 A | 1/2003 |
| JP | 2003-510158 A | 3/2003 |
| JP | 2003-116870 A | 4/2003 |
| JP | 2003-126104 A | 5/2003 |
| JP | 2003-126110 A | 5/2003 |
| JP | 2003-310627 A | 5/2003 |
| JP | 2003-530921 A | 10/2003 |
| JP | 2003-339730 A | 12/2003 |
| JP | 2004-147701 A | 5/2004 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-534451 A | 11/2005 |
| JP | 2006-6410 A | 1/2006 |
| JP | 2006-512149 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007-050181 A | 3/2007 |
| JP | 2007-229454 A | 9/2007 |
| JP | 2007-527747 A | 10/2007 |
| JP | 2008-508065 A | 3/2008 |
| JP | 2008-119250 A | 5/2008 |
| JP | 2008-521503 A | 6/2008 |
| JP | 2008-212679 A | 9/2008 |
| JP | 2008-536562 A | 9/2008 |
| JP | 2008-284374 A | 11/2008 |
| JP | 2009-511206 A | 3/2009 |
| JP | 2009-517181 A | 4/2009 |
| JP | 4262923 B2 | 5/2009 |
| JP | 2009-523567 A | 6/2009 |
| JP | 2009-236177 | 10/2009 |
| JP | 2009-254819 A | 11/2009 |
| JP | 2010-000336 A | 1/2010 |
| JP | 2010-514923 A | 5/2010 |
| JP | 2010-534522 A | 11/2010 |
| JP | 2010-540186 A | 12/2010 |
| JP | 2011-505198 A | 2/2011 |
| JP | 2012-235658 A | 11/2012 |
| JP | 5208761 B2 | 6/2013 |
| JP | D1339835 | 8/2015 |
| RU | 2154437 C1 | 8/2000 |
| RU | 22035 U1 | 3/2002 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 94/21183 A1 | 9/1994 |
| WO | WO 94/24949 A1 | 11/1994 |
| WO | WO 95/09572 A1 | 4/1995 |
| WO | WO 95/34259 A1 | 12/1995 |
| WO | WO 96/30885 A1 | 10/1996 |
| WO | WO 96/39086 A1 | 12/1996 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 A1 | 4/1999 |
| WO | WO 99/52489 A1 | 10/1999 |
| WO | WO 00/64358 A2 | 11/2000 |
| WO | WO 00/74585 A2 | 12/2000 |
| WO | WO 01/24713 A1 | 4/2001 |
| WO | WO 01/54590 A1 | 8/2001 |
| WO | WO 01/67970 A1 | 9/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO 2004/012615 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/098426 A1 | 11/2004 |
| WO | WO 2004/112618 A2 | 12/2004 |
| WO | WO 2005/117735 A1 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/101661 A2 | 9/2006 |

(56) References Cited

FOREIGN PATENT DOCUMENTS

| | | |
|---|---|---|
| WO | WO 2006/119139 A2 | 11/2006 |
| WO | WO 2006/119376 A2 | 11/2006 |
| WO | WO 2006/129465 A1 | 12/2006 |
| WO | WO 2007/008703 A2 | 1/2007 |
| WO | WO 2007/008710 A2 | 1/2007 |
| WO | WO 2007/038538 A1 | 4/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/120992 A2 | 10/2009 |
| WO | WO 2010/017149 A1 | 2/2010 |
| WO | WO 2010/068783 A1 | 6/2010 |
| WO | WO 2011/008672 A2 | 1/2011 |
| WO | WO 2011/052939 A2 | 5/2011 |
| WO | WO 2011/100321 A2 | 8/2011 |
| WO | WO 2011/144911 A1 | 11/2011 |
| WO | WO 2012/061722 A2 | 5/2012 |
| WO | WO 2012/128362 | 9/2012 |
| WO | WO 2012/135705 A1 | 10/2012 |
| WO | WO 2012/135721 A1 | 10/2012 |
| WO | WO 2013/018934 A1 | 2/2013 |
| WO | WO 2013/062978 A2 | 5/2013 |

OTHER PUBLICATIONS

European Search Report for 08782313.4, dated Feb. 15, 2013 (13 pages).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
European Examination Report for 08782313.4, dated Jan. 3, 2014 (12 pages).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/products/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www.megadyne.com/es_generator.php.
http://www.valleylab.com/product/es/generators/index.html.
Covidien 501(k) Summary Sonicision, dated Feb. 24, 2011 (7 pages).
Gerhard, Glen C., "Surgical Electrotechnology: Quo Vadis?," Biomedical Engineering, IEEE Transactions on , vol. BME-31, No. 12, pp. 787, 792, Dec. 1984.
Fowler, K.R., "A programmable, arbitrary waveform electrosurgical device," Engineering in Medicine and Biology Society, 1988. Proceedings of the Annual International Conference of the IEEE, vol., No., pp. 1324, 1325 vol. 3, Nov. 4-7, 1988.
LaCourse, J.R.; Vogt, M.C.; Miller, W.T., III; Selikowitz, S.M., "Spectral analysis interpretation of electro-surgical generator nerve and muscle stimulation," Biomedical Engineering, IEEE Transactions on , vol. 35, No. 7, pp. 505, 509, Jul. 1988.
U.S. Appl. No. 13/751,680, filed Jan. 28, 2013.

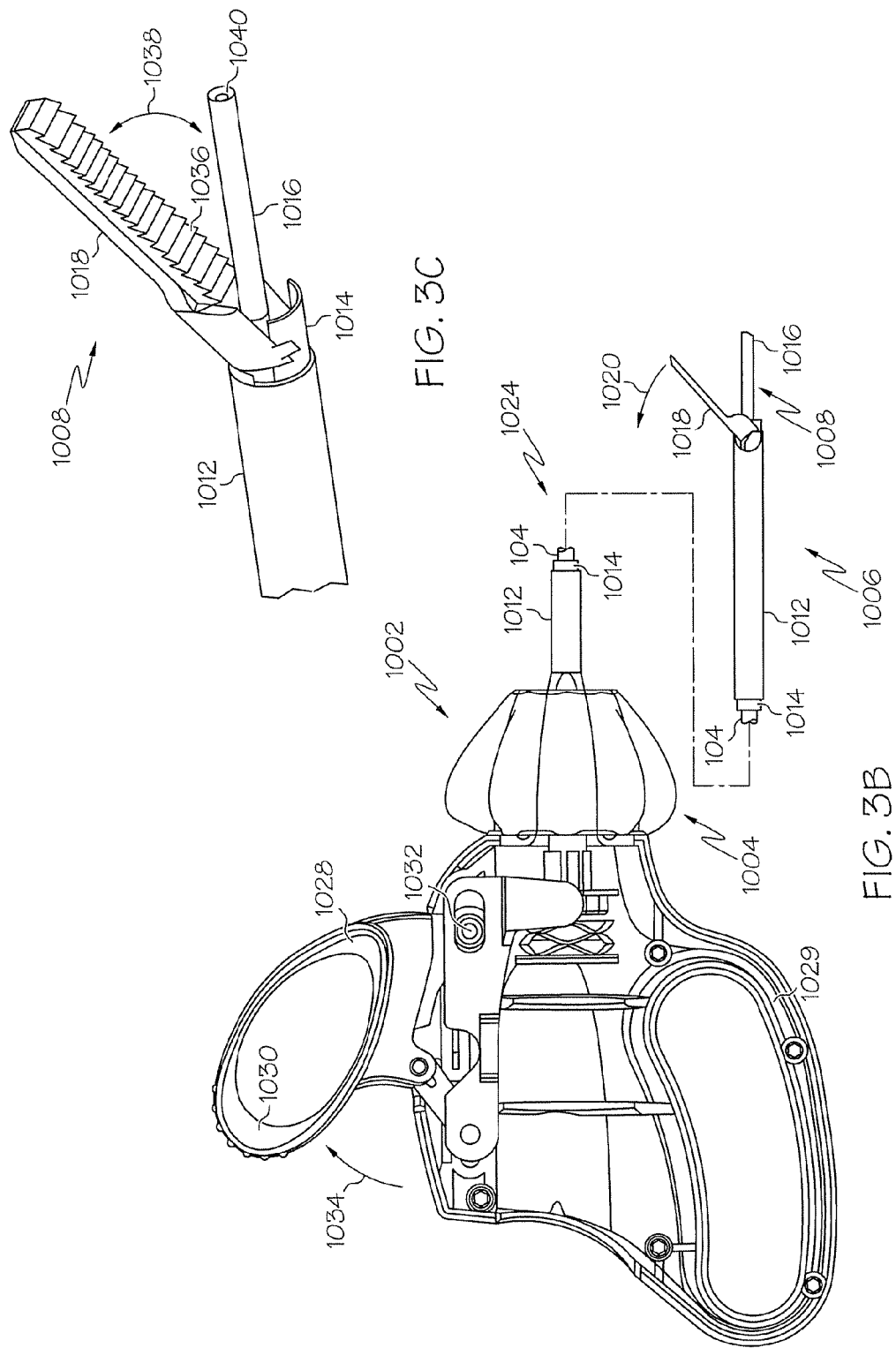

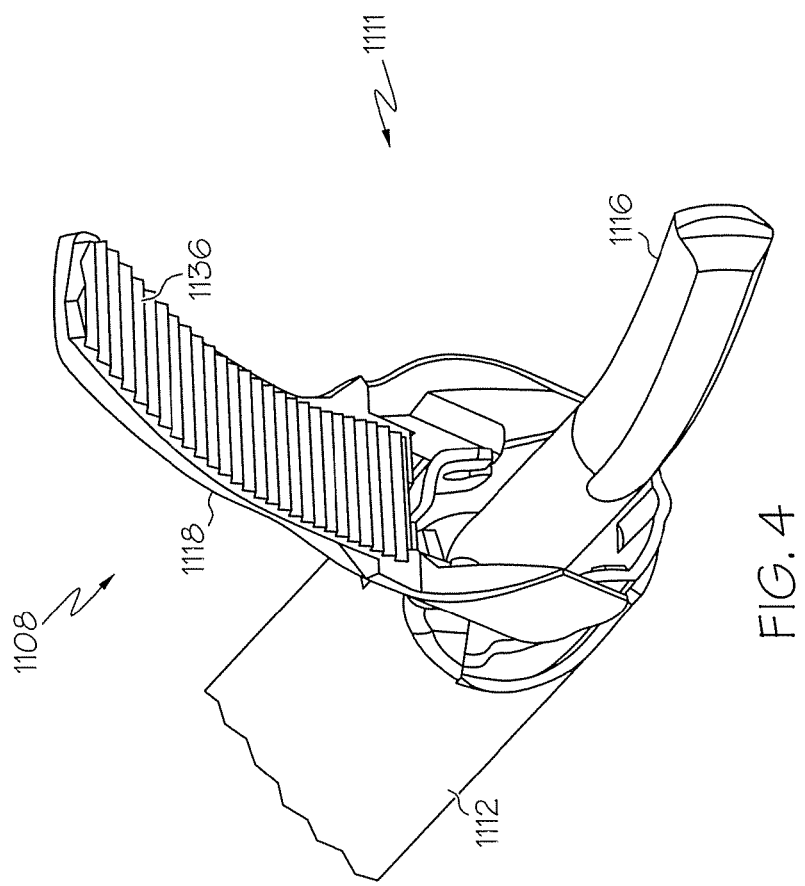

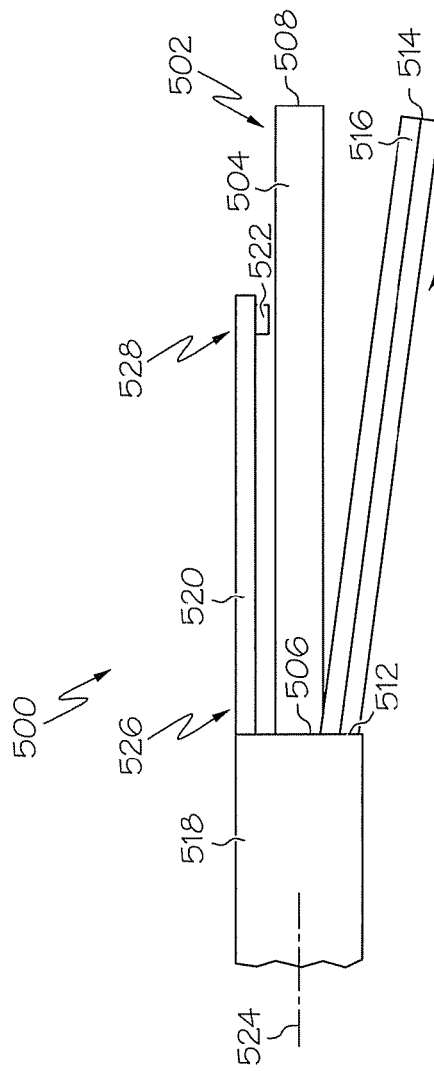
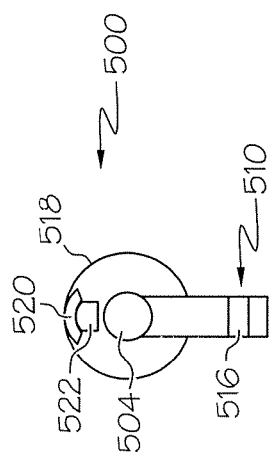
FIG. 22A
FIG. 22B

ULTRASONIC END EFFECTORS WITH INCREASED ACTIVE LENGTH

CROSS-REFERENCE TO RELATED APPLICATIONS

This application is a divisional of copending U.S. patent application Ser. No. 11/881,662 entitled "ULTRASONIC END EFFECTORS WITH INCREASED ACTIVE LENGTH," filed on Jul. 27, 2007, which is herein entirely incorporated by reference.

BACKGROUND

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate, coagulate or cauterize tissue, or to separate muscle tissue off bone. Ultrasonic instruments utilizing solid core technology are particularly advantageous because of the amount of ultrasonic energy that may be transmitted from an ultrasonic transducer, through a transmission component or waveguide, to the surgical end effector. Such instruments may be used for open or minimally invasive surgical procedures, such as endoscopic or laparoscopic surgical procedures, wherein the end effector is passed through a trocar to reach the surgical site.

Activating or exciting the single or multiple-element end effector of such instruments at ultrasonic frequencies induces longitudinal, transverse or torsional vibratory movement that generates localized heat within adjacent tissue, facilitating both cutting and coagulation. Because of the nature of ultrasonic instruments, a particular ultrasonically actuated end effector may be designed to perform numerous functions, including, for example, cutting, coagulating, scraping, or lifting tissue with or without the assistance of a clamping assembly.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic transmission component such as a waveguide extending from the transducer section to the surgical end effector. The waveguides and end effectors are most preferably designed to resonate at the same frequency as the transducer. Therefore, when an end effector is attached to a transducer the overall system frequency is the same frequency as the transducer itself.

The zero to peak amplitude of the longitudinal ultrasonic vibration at the tip, d, of the end effector behaves as a simple sinusoid at the resonant frequency as given by:

$$d = A \sin(\omega t)$$

where:
$\omega$=the radian frequency which equals $2\pi$ times the cyclic frequency, f and
A=the zero-to-peak amplitude.

The longitudinal excursion is defined as the peak-to-peak (p-t-p) amplitude, which is just twice the amplitude of the sine wave or 2A.

Solid core ultrasonic instruments may be divided into two types, single element end effector devices and multiple-element end effector. Single element end effector devices include instruments such as blades, scalpels, hooks and/or ball coagulators. Multiple-element end effectors may include a mechanism to press tissue against an ultrasonic blade. Multiple-element end effectors comprise clamping scalpels and/or clamping coagulators or any combination of a clamping assembly with a single element end effector. Multiple-element end effectors may be employed when substantial pressure may be necessary to effectively couple ultrasonic energy to the tissue. Ultrasonic clamp coagulators, for example, may be employed for cutting and coagulating tissue, particularly loose and unsupported tissue. Multiple-element end effectors that include an ultrasonic blade in conjunction with a clamp apply a compressive or biasing force to the tissue to promote faster coagulation and cutting of the tissue.

Ultrasonic clamp coagulators provide an improved ultrasonic surgical instrument for cutting/coagulating tissue, particularly loose and unsupported tissue, wherein the ultrasonic blade is employed in conjunction with a clamp for applying a compressive or biasing force to the tissue, whereby faster coagulation and cutting of the tissue are achieved.

Ultrasonic instruments are designed and manufactured such that the maximum amplitude of the longitudinal ultrasonic vibration (i.e., the anti-node) is localized at or near the distal end of the end effector in order to maximize longitudinal excursion of the distal end. The active length of an ultrasonic instrument is generally defined as the distance from the distal end of the end effector (where ultrasonic displacement is at a maximum) to a proximal location along the end effector where ultrasonic displacement decreases below a predetermined level approaching a node (where ultrasonic displacement is at a minimum). The length segment of an end effector surrounding a node where ultrasonic displacement is below a predetermined level is defined as the nodal gap. Accordingly, the nodal gap is the length in the vicinity of the node that has insufficient displacement to generate the necessary heat for efficient and/or effective cutting and/or coagulation.

As used herein, the term "nodal gap" refers to the length segment of an end effector that has insufficient ultrasonic displacement to generate the necessary heat for efficient and/or effective cutting and/or coagulation. As used herein, the term "nodal gap region" refers to the area in the vicinity of a node and may refer to the area on or in an end effector or the area adjacent to the end effector in the vicinity of a node. As used herein, the term "nodal energy gap" refers to the condition where insufficient ultrasonic displacement to generate the necessary heat for efficient and/or effective cutting and/or coagulation is produced in the vicinity of a node.

The relatively low displacements in the vicinity of the node result in lower amounts of heat being delivered to tissue in contact with the end effector in the nodal gap region than in other regions of the end effector. Accordingly, in the nodal gap region, the tissue in contact with the blade does not get directly heated. As a result, the tissue is not effectively cut and/or coagulated, and the tissue may stick to the end effector in the nodal gap region or may simply be desiccated without being transected. It would be desirable to provide an end effector for use in an ultrasonic surgical instrument that effectively eliminates the nodal gap.

SUMMARY

In one embodiment, a surgical instrument, comprises a transducer configured to produce vibrations along a longitudinal axis at a predetermined frequency. An ultrasonic blade extends along the longitudinal axis coupled to the transducer. The ultrasonic blade comprises a body having a proximal end and a distal end, wherein the distal end is movable along the longitudinal axis by the vibrations produced by the transducer. A non-vibrating clamp arm assembly has a proximal end and a distal end and pivotally positioned adjacent to the body. The clamp arm assembly is pivotally moveable from an open position to a closed position. The non-vibrating clamp arm assembly comprises a proximal tissue pad segment, a distal tissue pad segment, and a tissue pad insert segment positioned between the proximal tissue pad segment and the distal tissue pad segment.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

FIG. 3B illustrates one embodiment of an ultrasonic surgical instrument comprising a multiple-element end effector.

FIG. 3C illustrates a detail perspective view of one embodiment of a multiple-element end effector as shown in FIG. 3B.

FIG. 4 is a perspective view of one embodiment of a multiple-element end effector.

FIGS. 7-9 illustrate various embodiments of a single-element end effector comprising insert segments having different specific acoustic impedance values than the main portion of the end effector, where:

FIG. 7 is a side view of one embodiment of a single-element end effector comprising one insert segment;

FIG. 9 is a side view of one embodiment of a single-element end effector comprising three insert segments.

FIG. 10 is a graph of rectified ultrasonic displacement as a function of length/distance for an end effector formed entirely of stainless steel;

Figure 11:
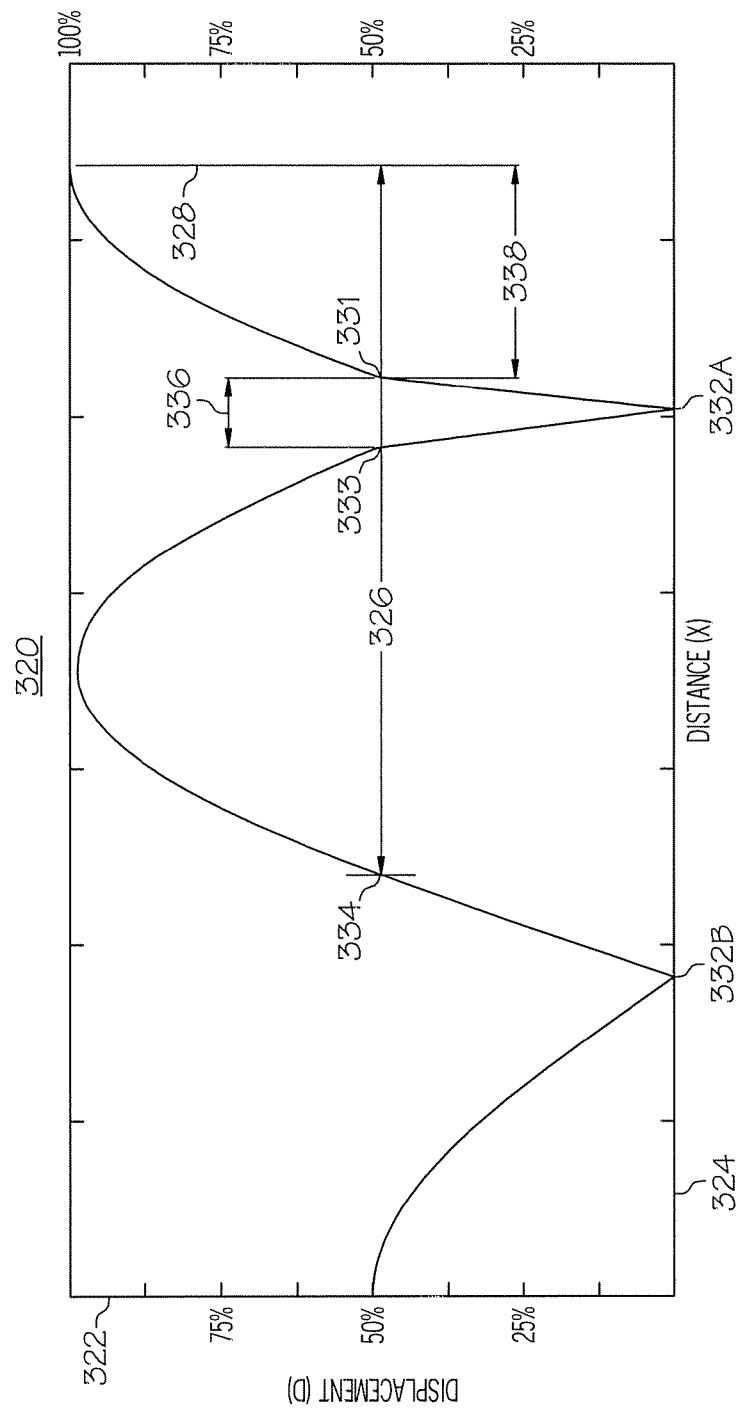
Figure 12:
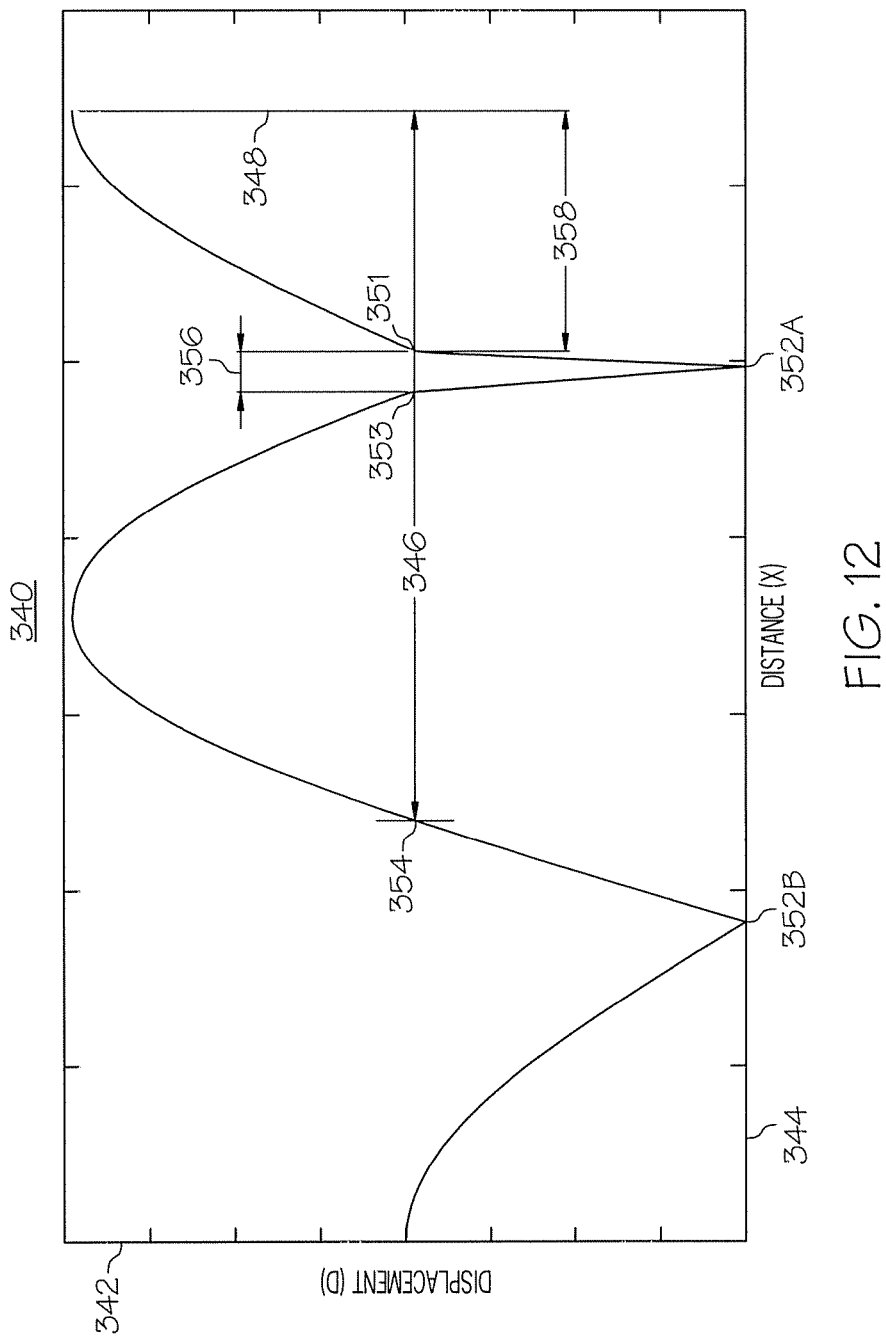

FIG. 11 is a graph of rectified ultrasonic displacement as a function of length/distance for a stainless steel end effector comprising an aluminum insert segment having a cross-sectional area matching the cross-sectional area of the stainless steel portion; and FIG. 12 is a graph of rectified ultrasonic displacement as a function of length/distance for a stainless steel end effector comprising an aluminum insert segment having a cross-sectional area half the cross-sectional area of the stainless steel portion.

Figure 13:
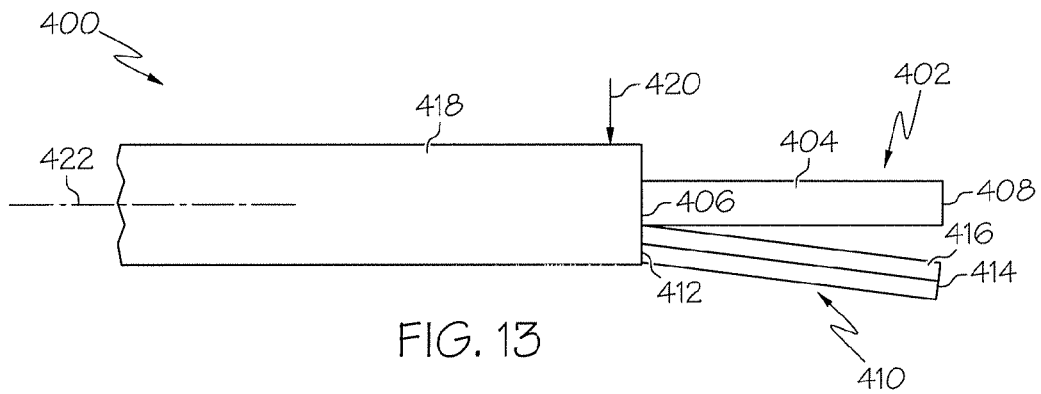
Figure 14:
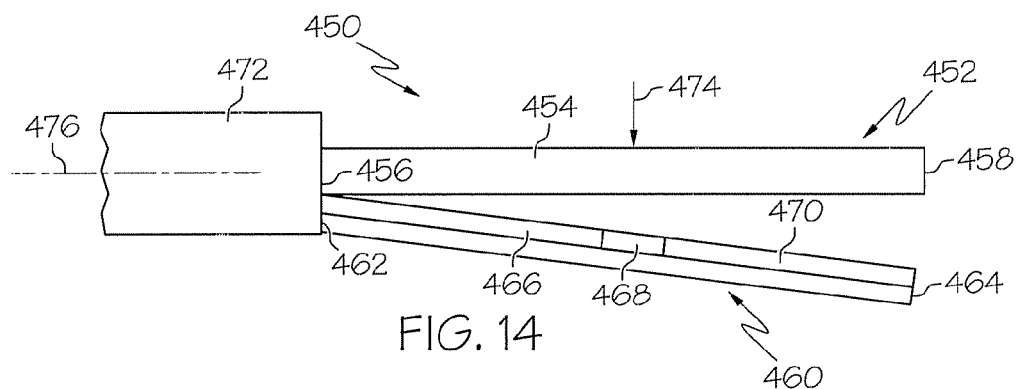
Figure 15:
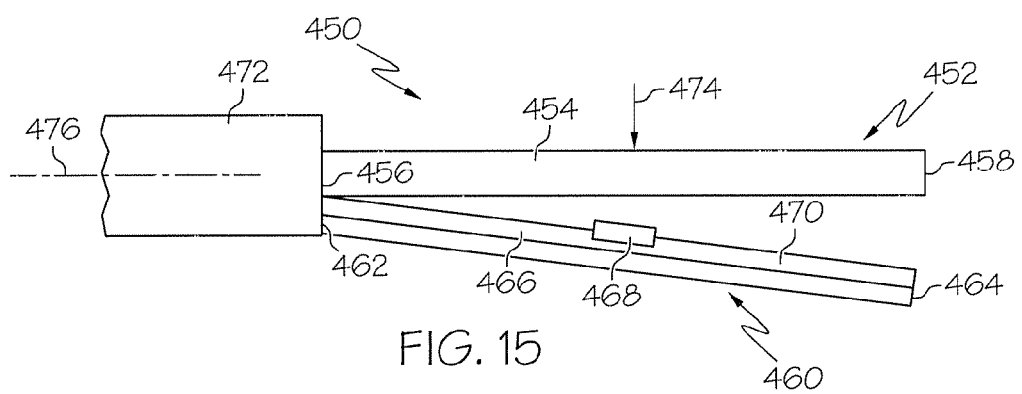
Figure 16:
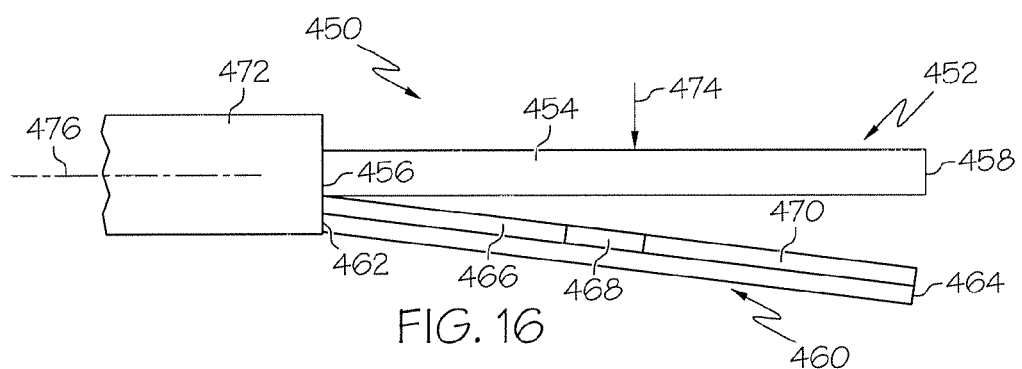
Figure 17:
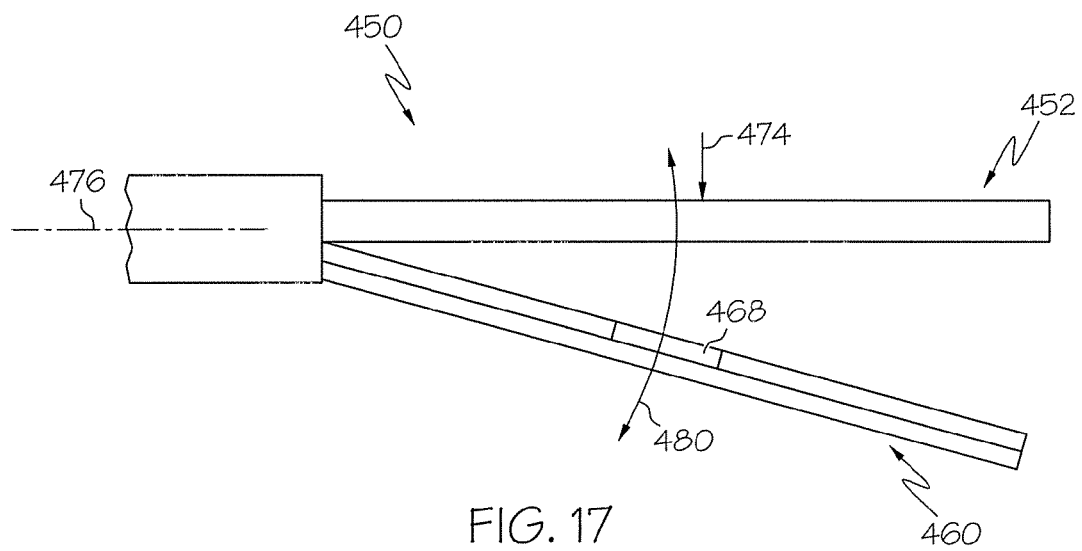
Figure 18:
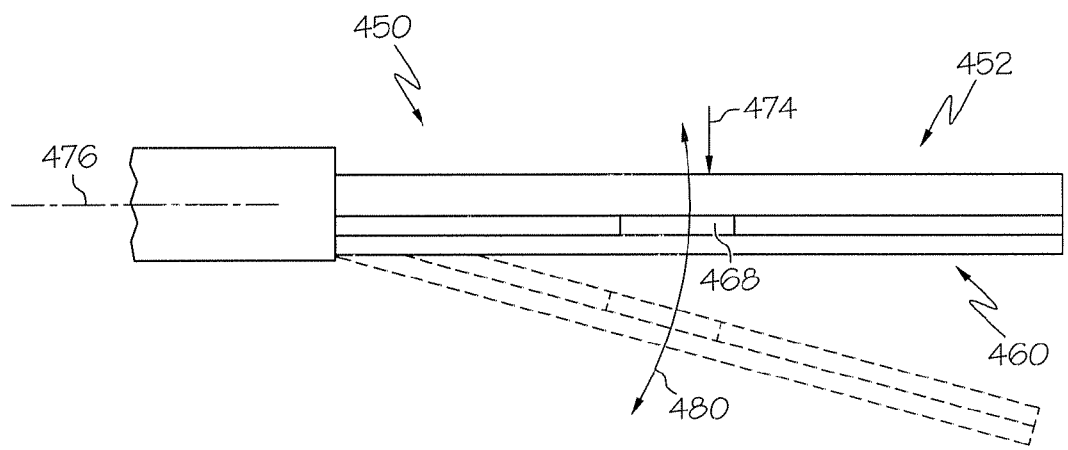

FIGS. 13-18 illustrate various embodiments of an ultrasonic surgical instrument, where:

FIG. 13 is a partial side view of one embodiment of an ultrasonic surgical instrument in a conventional configuration without an insert segment;

FIG. 14 is a partial side view of one embodiment of an ultrasonic surgical instrument having an insert segment positioned in a clamp arm assembly in a nodal gap region;

FIG. 15 is a partial side view of one embodiment of an ultrasonic surgical instrument having a raised insert segment positioned in a clamp arm assembly;

FIG. 16 is a partial side view of one embodiment of an ultrasonic surgical instrument having an insert segment positioned in a clamp arm assembly offset from a node;

FIG. 17 is a partial side view of one embodiment of an ultrasonic surgical instrument having an insert segment positioned in a clamp arm assembly in an open position; and FIG. 18 is a partial side view of one embodiment of an ultrasonic surgical instrument having an insert segment positioned in a clamp arm assembly in a closed position.

Figure 19:
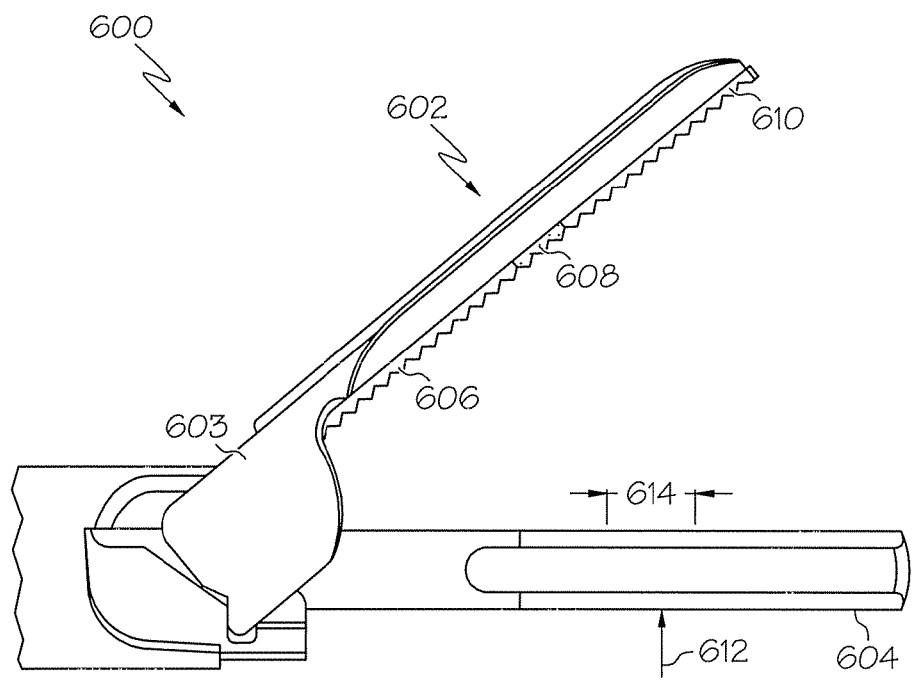

FIG. 19 is a partial side view of one embodiment of a multiple-element end effector comprising a clamp arm assembly and a surgical blade.

Figure 20:
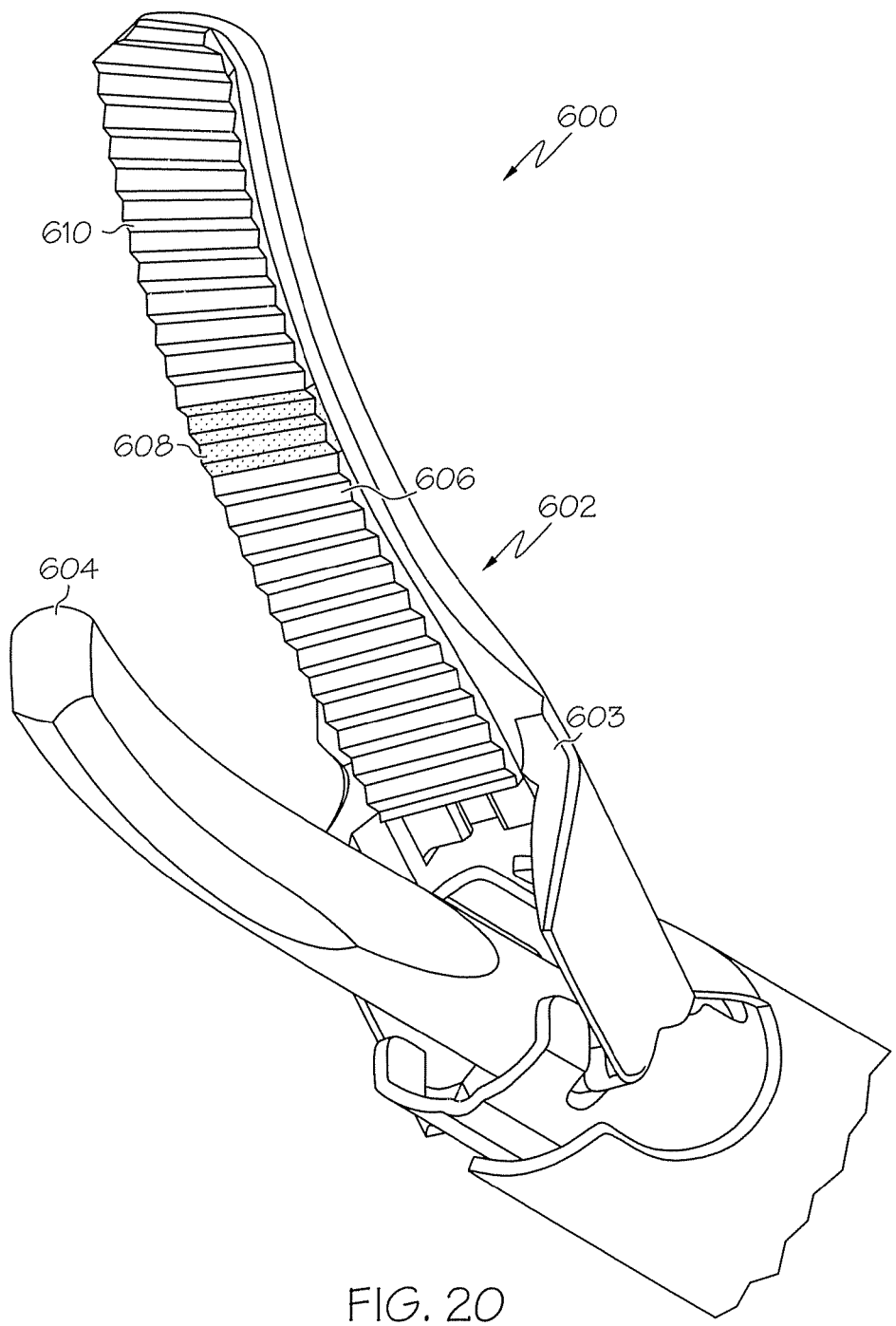

FIG. 20 is a perspective view of one embodiment of a multiple-element end effector as illustrated in FIG. 19.

Figure 21:
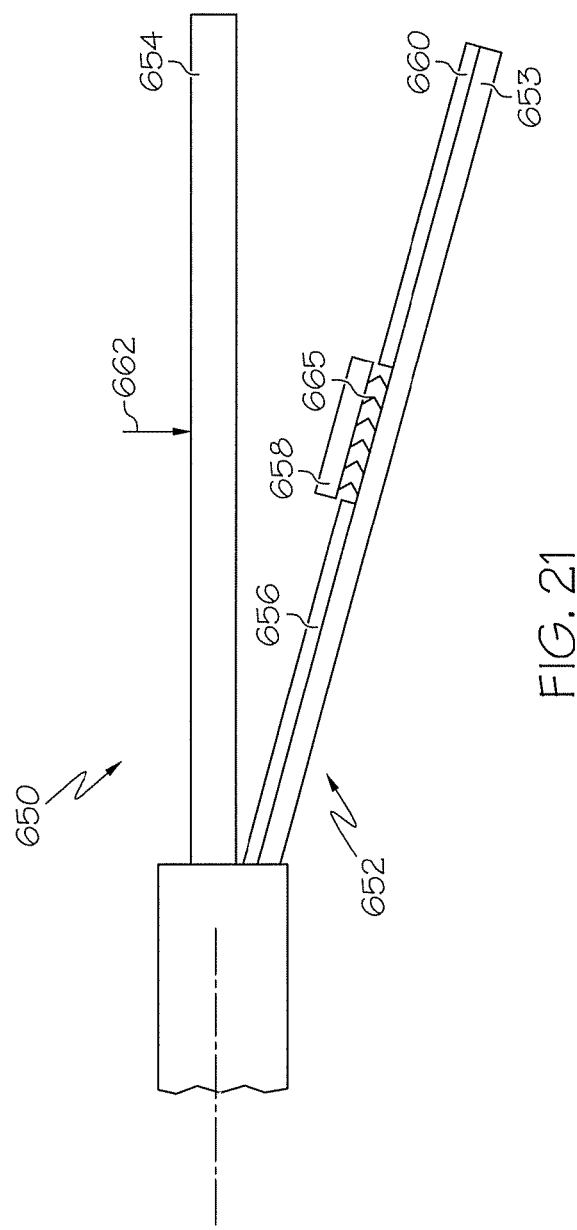

FIG. 21 is a partial side view of one embodiment of a multiple-element end effector comprising a clamp arm assembly and a surgical blade.

Figure 23A:
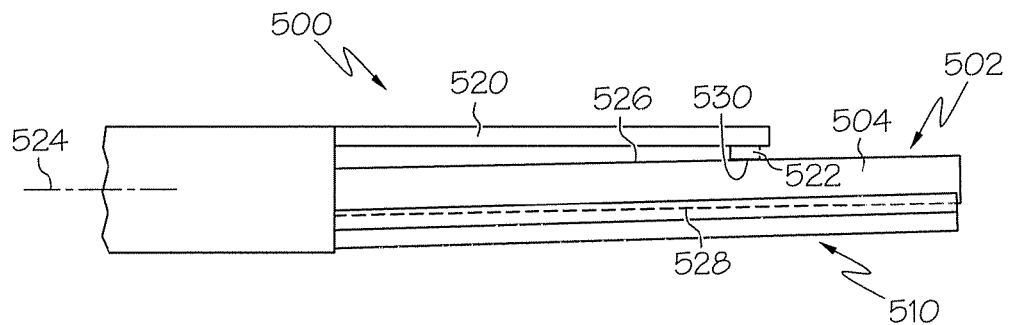
Figure 23B:
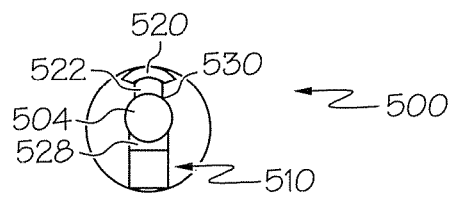
Figure 24A:
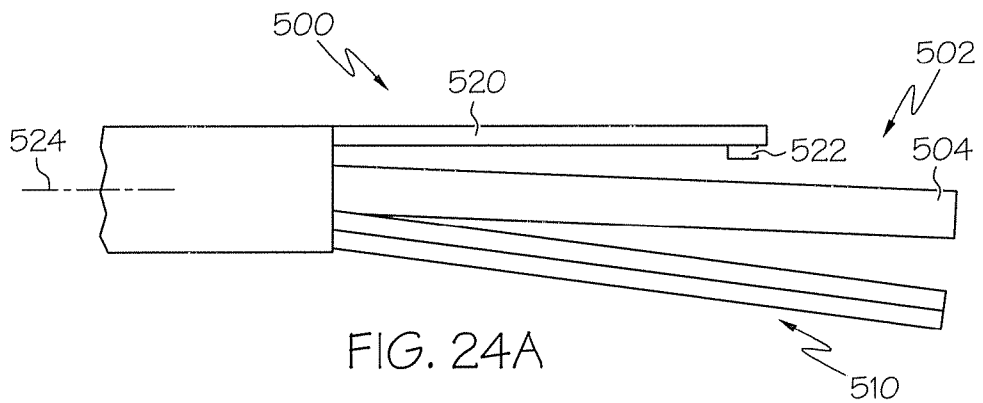
Figure 24B:
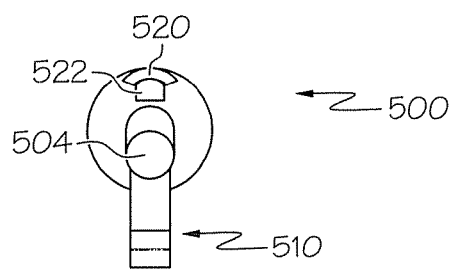
Figure 25A:
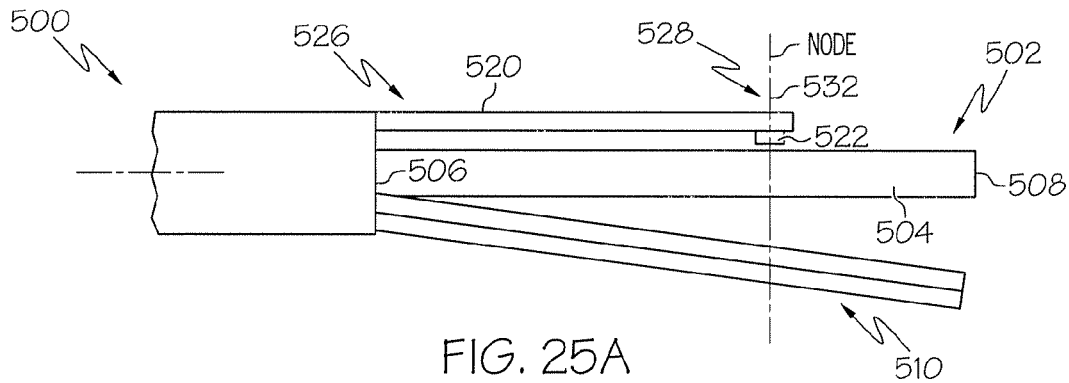
Figure 25B:
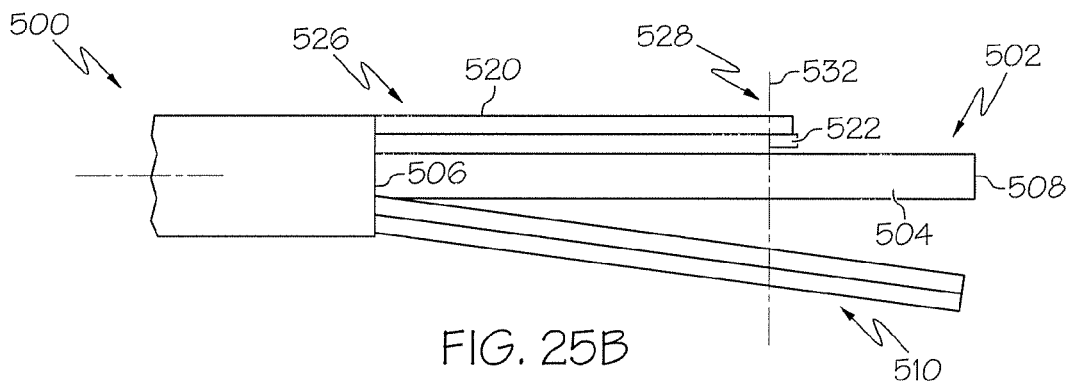
Figure 25C:
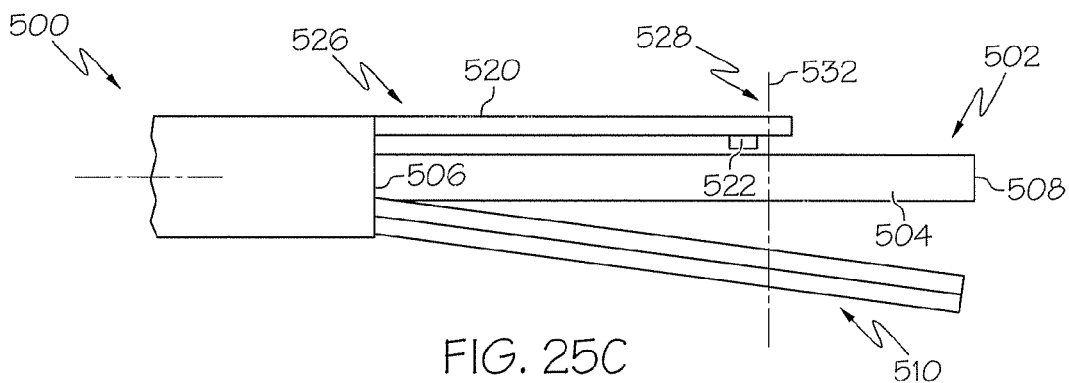
Figure 25D:
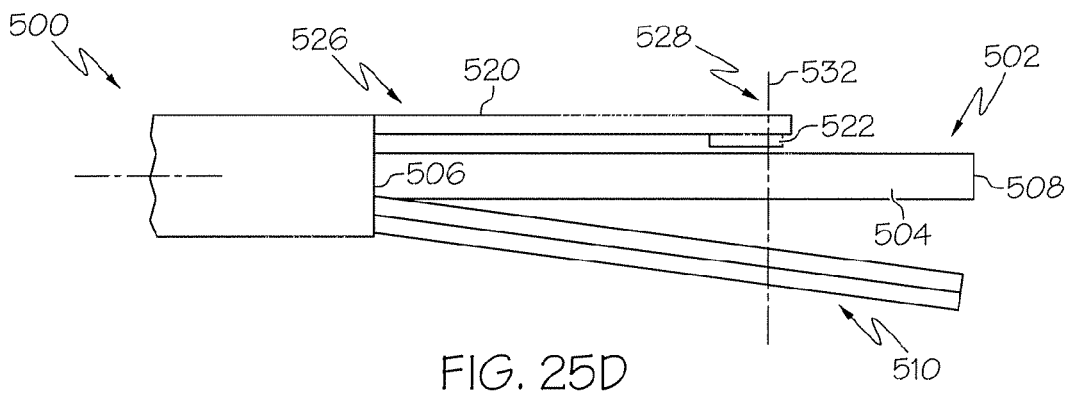

FIGS. 22-25 illustrate various embodiments of an ultrasonic surgical instrument comprising a pad for generating frictional heat when engaged with an operating surgical blade, where:

FIG. 22A is a partial side view of one embodiment of an ultrasonic surgical instrument in an open position and inactive and having a pad positioned toward the distal end of an extension member;

FIG. 22B is an end view of one embodiment of the ultrasonic surgical instrument of FIG. 22A;

FIG. 23A is a partial side view of one embodiment of an ultrasonic surgical instrument in a closed position and activated and having a pad positioned toward the distal end of an extension member;

FIG. 23B is an end view of one embodiment of the ultrasonic surgical instrument of FIG. 23A;

FIG. 24A is a partial side view of one embodiment of an ultrasonic surgical instrument in an open position and activated and having a pad positioned toward the distal end of an extension member;

FIG. 24B is an end view of one embodiment of the ultrasonic surgical instrument of FIG. 24A;

FIG. 25A is a partial side view of one embodiment of an ultrasonic surgical instrument in an open position and inactive with a pad positioned on an extension member and located at a node;

FIG. 25B is a partial side view of one embodiment of an ultrasonic surgical instrument in an open position and inactive with a pad positioned on an extension member and offset distally from a node;

FIG. 25C is a partial side view of one embodiment of an ultrasonic surgical instrument in an open position and inactive with a pad positioned on an extension member and offset proximally from a node;

FIG. 25D is a partial side view of one embodiment of an ultrasonic surgical instrument in an open position and inactive with a pad of a different length positioned on an extension member and spanning a node.

Figure 26A:
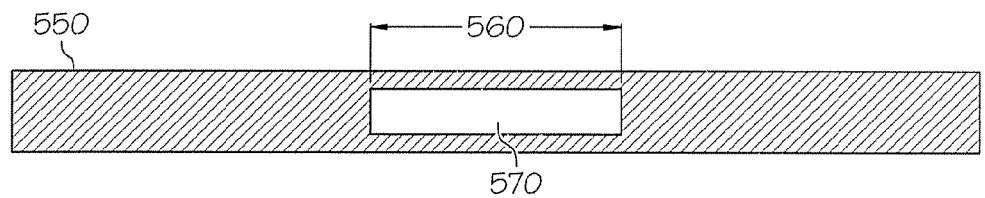

FIGS. 26A-E illustrate various embodiments of single-element end effectors, where:

FIG. 26A is a cross-sectional side view of a single-element end effector comprising an internal cavity or bore.

Figure 26B:
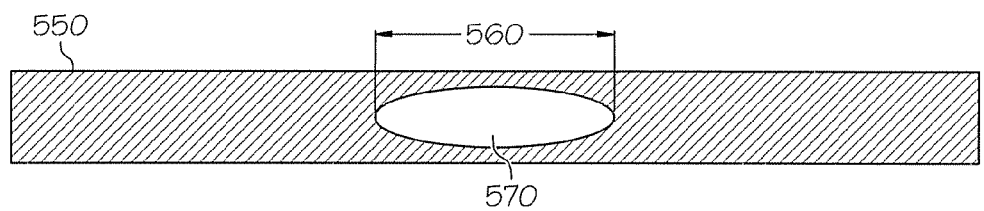

FIG. 26B is a cross-sectional side view of a single-element end effector comprising an internal cavity or bore.

Figure 26C:
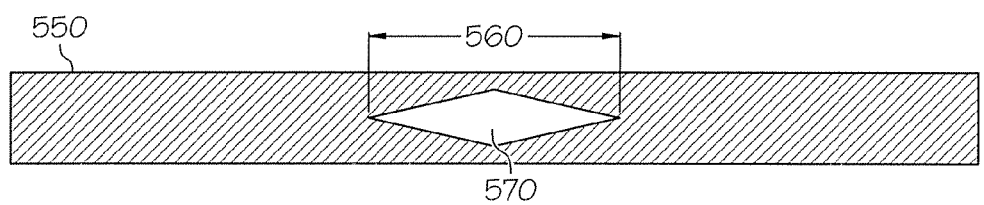

FIG. 26C is a cross-sectional side view of a single-element end effector comprising an internal cavity or bore.

Figure 26D:
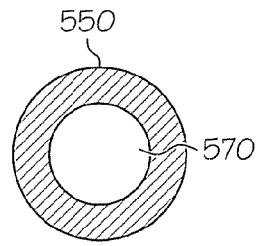

FIG. 26D is a cross-sectional end view of a single-element end effector comprising an internal cavity or bore.

Figure 26E:
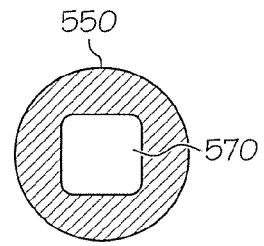

FIG. 26E is a cross-sectional end view of a single-element end effector comprising an internal cavity or bore.

Figure 27:
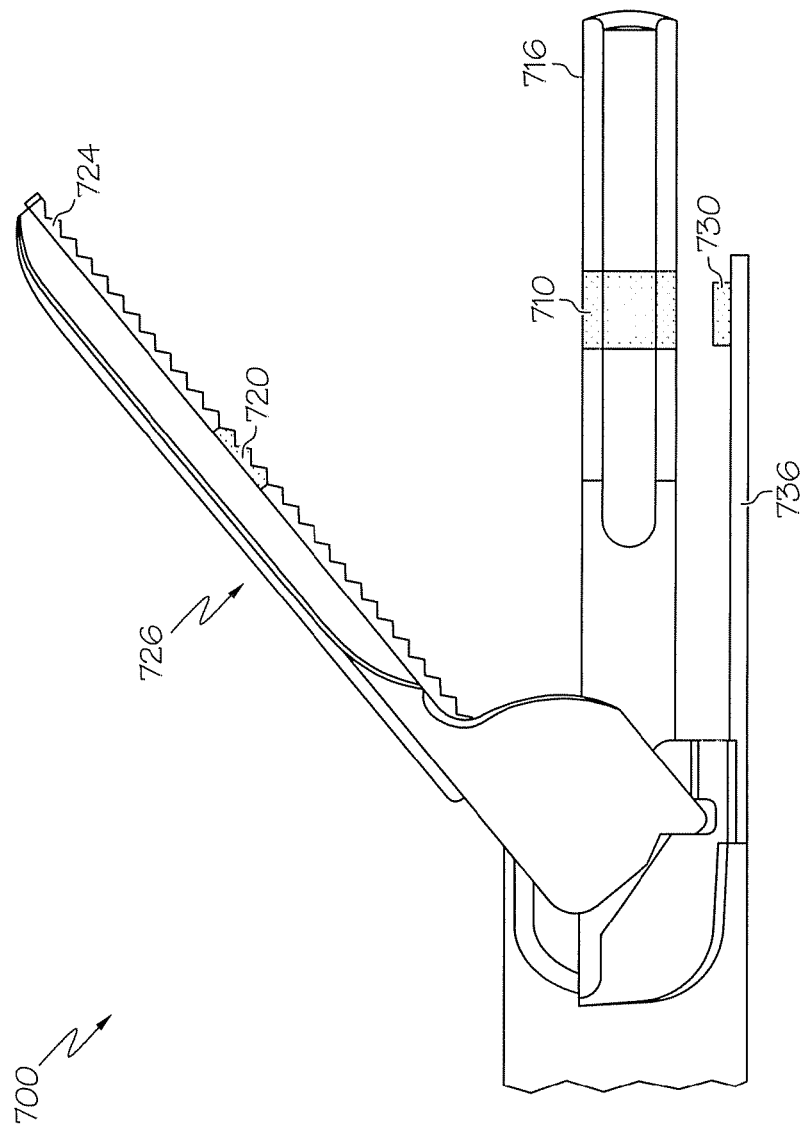

FIG. 27 is a partial side view of one embodiment of an ultrasonic end effector having an insert segment positioned in a blade, a tissue pad insert segment positioned in the tissue pad of a clamp arm assembly and a pad positioned on an extension member.

DESCRIPTION

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments, end effector and blade configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

The various embodiments relate, in general, to ultrasonic surgical end effectors for use in surgical instruments and, more particularly, to an ultrasonic surgical end effector with improved elevator, cutting and coagulation features in the nodal gap region. The various embodiments relate, in general, to ultrasonic surgical end effectors and instruments for improved bone and tissue removal, aspiration, and coagulation features. An end effector according to various embodiments is of particular benefit, among others, in procedures wherein it is desirable to remove bone and/or tissue while controlling bleeding, for example, removing muscle tissue from bone, due to its cutting and coagulation characteristics. The end effector, however, may be useful for general soft tissue cutting and coagulation. The end effector may be straight or curved, and useful for either open or laparoscopic applications. An end effector according to various embodiments may be useful in spine surgery, especially to assist in posterior access in removing muscle from bone. An end effector according to the various embodiments may reduce the user force required to remove muscle from bone and, in various embodiments, may be useful to simultaneously hemostatically seal or cauterize the tissue. Reducing the force to operate the surgical instrument may reduce user fatigue, improve precision and reduce unwanted tissue damage. A variety of different end effector configurations are disclosed which may be useful for both open and laparoscopic applications.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218B1, 6,283,981 B1, and 6,325,811 B1, for example, are incorporated herein by reference in their entirety. These references disclose ultrasonic surgical instrument designs and blade designs where a longitudinal mode of the blade is excited. Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

In one general aspect, the various embodiments are directed to an end effector for use with an ultrasonic surgical instrument. The end effector comprises a first portion having a first specific acoustic impedance value and a second portion having a second specific acoustic impedance value. The second specific acoustic impedance value is less than the first specific acoustic impedance value.

In another general aspect, the various embodiments are directed to an end effector for use with an ultrasonic surgical instrument. The end effector comprises a distal end segment comprised of a first acoustic impedance material, a distal insert segment comprised of a second acoustic impedance material, a middle insert segment comprised of a third acoustic impedance material, a proximal insert segment comprised of a fourth acoustic impedance material, and a proximal end segment comprised of a fifth acoustic impedance material.

In yet another general aspect, the various embodiments are directed to an end effector for use with an ultrasonic surgical instrument. The end effector comprises a proximal end segment, a distal end segment, and an insert segment wherein the insert segment is located between the proximal end segment and the distal end segment. The insert segment of the end effector comprises a lossy material or a material having a specific acoustic impedance value different than the specific acoustic impedance values of the proximal end segment and the distal end segment.

In still another general aspect, the various embodiments are directed to an ultrasonic surgical blade that comprises a plurality of segments. At least one of the plurality of segments is configured to fill and/or narrow a nodal energy gap. In yet another general aspect, the various embodiments are directed to an ultrasonic surgical blade comprising a single material. The specific acoustic impedance of the blade changes along the length.

In still another general aspect, the various embodiments are directed to a surgical instrument that comprises a transducer configured to produce vibrations along a longitudinal axis at a predetermined frequency. An ultrasonic blade extends along the longitudinal axis coupled to the transducer. The blade includes a body having a proximal end and a distal end. The distal end is movable along the longitudinal axis by the vibrations produced by the transducer. A non-vibrating clamp arm assembly having a proximal end and a distal end is pivotally positioned adjacent to the body. The clamp arm assembly is pivotally moveable from an open position to a closed position. The non-vibrating clamp arm assembly comprises a proximal tissue pad segment, a distal tissue pad segment, and a tissue pad insert segment positioned between the proximal tissue pad segment and the distal tissue pad segment.

In yet another general aspect, the various embodiments are directed to surgical instrument that comprises a transducer configured to produce vibrations along a longitudinal axis as a predetermined frequency. An ultrasonic blade extends along the longitudinal axis coupled to the transducer. The blade includes a body having a proximal end and a distal end. The distal end is movable along the longitudinal axis by the vibrations produced by the transducer. An extension member comprises a proximal end and a distal end is disposed adjacent to the body. The extension member further comprises a pad positioned on the distal end of the extension member and located between the body and the distal end of the extension member.

In still another general aspect, the various embodiments are directed to surgical instrument that comprises a transducer configured to produce vibrations along a longitudinal axis at a predetermined frequency. An ultrasonic blade extends along the longitudinal axis coupled to the transducer. The blade includes a body having a proximal end and a distal end. The distal end is movable along the longitudinal axis by the vibrations produced by the transducer. A protective sheath comprising a proximal end and a distal end is disposed adjacent to the body. The protective sheath further comprises a pad positioned on the distal end of the protective sheath and located between the body and the distal end of the protective sheath.

Figure 1:
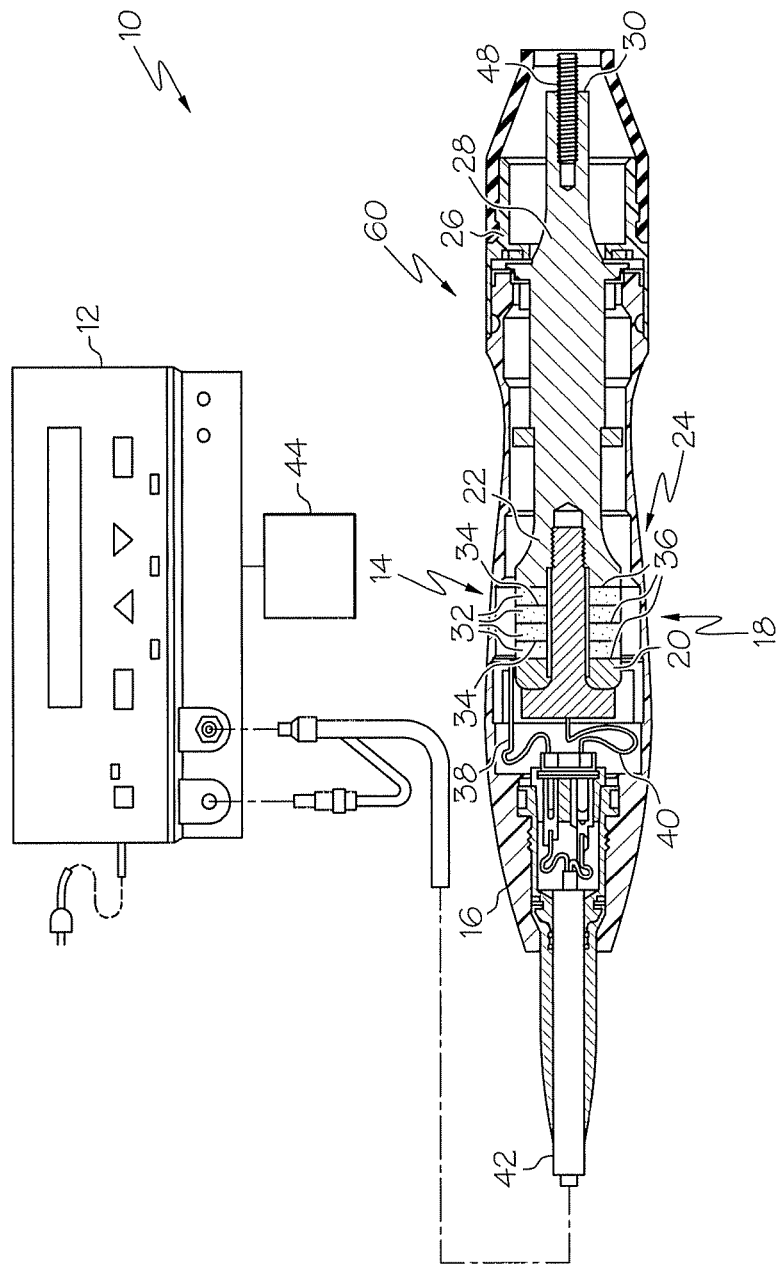
FIG. 1 illustrates one embodiment of an ultrasonic system.

FIG. 1 illustrates one embodiment of ultrasonic system 10. One embodiment of ultrasonic system 10 comprises ultrasonic signal generator 12 coupled to ultrasonic transducer 14, and hand piece assembly 60 comprising hand piece housing 16. The distal end of ultrasonic transducer 14 is adapted to couple to an ultrasonic transmission assembly comprising an elongated transmission component coupled to a single element or multiple-element end effector. Ultrasonic transducer 14, which is known as a "Langevin stack", generally includes transduction portion 18, first resonator or end-bell 20, and second resonator or fore-bell 22, and ancillary components. The length of ultrasonic transducer 14 is preferably an integral number of one-half system wavelengths (nλ/2) as will be described in more detail herein. Acoustic assembly 24 includes ultrasonic transducer 14, nose cone 26, velocity transformer 28, and surface 30 adapted to couple to an ultrasonic transmission assembly.

It will be appreciated that the terms "proximal" and "distal" are used herein with reference to a clinician gripping the hand piece assembly 60. Thus, the end effector is distal with respect to the more proximal hand piece assembly 60. It will be further appreciated that, for convenience and clarity, spatial terms such as "top" and "bottom" also are used herein with respect to the clinician gripping hand piece assembly 60. However, surgical instruments are used in many orientations and positions, and these terms are not intended to be limiting and absolute.

The distal end of end-bell 20 is connected to the proximal end of transduction portion 18, and the proximal end of fore-bell 22 is connected to the distal end of transduction portion 18. Fore-bell 22 and end-bell 20 have a length determined by a number of variables, including the thickness of transduction portion 18, the density and modulus of elasticity of the material used to manufacture end-bell 20 and fore-bell 22, and the resonant frequency of the ultrasonic transducer 14. Fore-bell 22 may be tapered inwardly from its proximal end to its distal end to amplify the ultrasonic vibration amplitude as velocity transformer 28, or alternately may have no amplification. A suitable vibrational frequency range may be about 20 Hz to 120 kHz and a well-suited vibrational frequency range may be about 30-100 kHz and a suitable operational vibrational frequency may be approximately 55.5 kHz, for example.

Piezoelectric elements 32 may be fabricated from any suitable material, such as, for example, lead zirconate-titanate, lead meta-niobate, lead titanate, or other piezoelectric ceramic material. Each of positive electrodes 34, negative electrodes 36, and piezoelectric elements 32 has a bore extending through the center. Positive and negative electrodes 34 and 36 are electrically coupled to wires 38 and 40, respectively. Wires 38 and 40 are encased within cable 42 and electrically connectable to ultrasonic signal generator 12 of ultrasonic system 10.

Ultrasonic transducer 14 of acoustic assembly 24 converts the electrical signal from ultrasonic signal generator 12 into mechanical energy that results in primarily longitudinal vibratory motion of ultrasonic transducer 14 and an end effector at ultrasonic frequencies. A suitable generator is available as model number GEN04, from Ethicon Endo-Surgery, Inc., Cincinnati, Ohio. When acoustic assembly 24 is energized, a vibratory motion standing wave is generated through acoustic assembly 24. The amplitude of the vibratory motion at any point along acoustic assembly 24 may depend upon the location along acoustic assembly 24 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where motion is maximal). The distance between an anti-node and its nearest node is one-quarter wavelength (λ/4).

Wires 38 and 40 transmit an electrical signal from ultrasonic signal generator 12 to positive electrodes 34 and negative electrodes 36. Piezoelectric elements 32 are energized by the electrical signal supplied from ultrasonic signal generator 12 in response to a triggering mechanism, for example foot switch 44, to produce an acoustic standing wave in acoustic assembly 24. The electrical signal causes disturbances in piezoelectric elements 32 in the form of repeated small displacements resulting in large compression forces within the material. The repeated small displacements cause piezoelectric elements 32 to expand and contract in a continuous manner along the longitudinal axis of the voltage gradient, producing longitudinal waves of ultrasonic energy. The ultrasonic energy is transmitted through acoustic assembly 24 to an end effector via an ultrasonic transmission component such as an ultrasonic transmission waveguide.

In order for acoustic assembly 24 to deliver energy to an end effector, all components of acoustic assembly 24 must be acoustically coupled to the end effector. The distal end of ultrasonic transducer 14 may be acoustically coupled at surface 30 to the proximal end of an ultrasonic transmission waveguide by a threaded connection such as stud 48.

The components of acoustic assembly 24 are preferably acoustically tuned such that the length of any assembly is an integral number of one-half wavelengths (nλ/2), where the wavelength λ is the wavelength of a pre-selected or operating longitudinal vibration drive frequency $f_d$ of acoustic assembly 24, and where n is any positive integer. It is also contemplated that acoustic assembly 24 may incorporate any suitable arrangement of acoustic elements.

Figure 2:
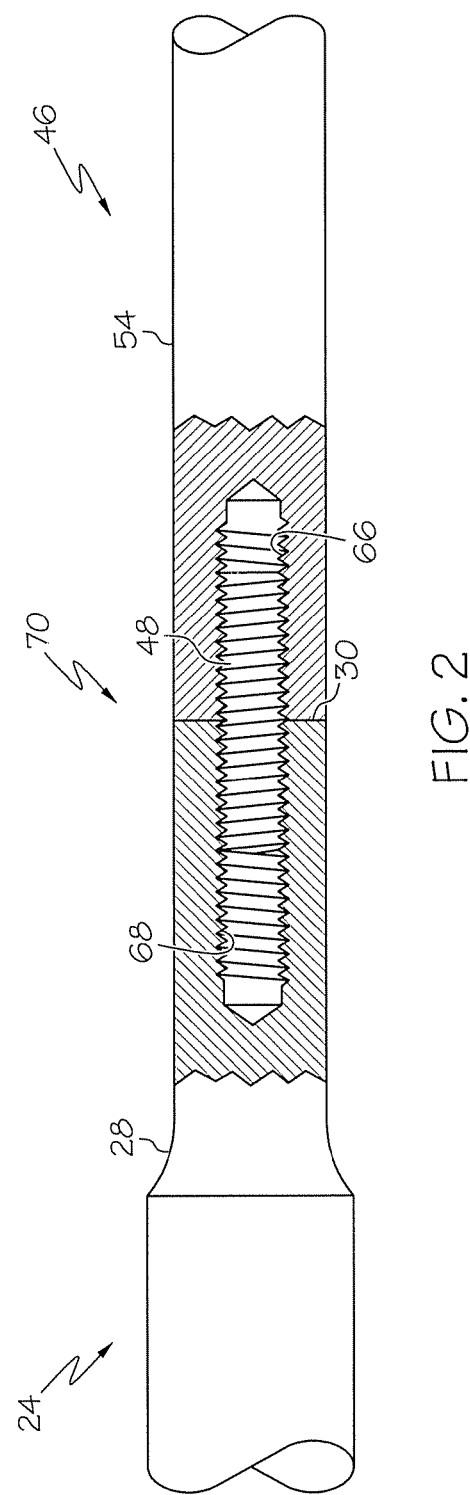
FIG. 2 illustrates one embodiment of a connection union/joint for an ultrasonic instrument.

FIG. 2 illustrates one embodiment of a connection union/joint 70 for an ultrasonic instrument between acoustic assembly 24 and an ultrasonic transmission component such as an ultrasonic transmission waveguide. Connection union/joint 70 may be formed between attachment post 54 of an ultrasonic transmission waveguide and surface 30 of velocity transformer 28 at the distal end of acoustic assembly 24. The proximal end of attachment post 54 comprises a female threaded substantially cylindrical recess 66 to receive a portion of threaded stud 48 therein. The distal end of velocity transformer 28 also may comprise a female threaded substantially cylindrical recess 68 to receive a portion of threaded stud 48. The recesses 66 and 68 are substantially circumferentially and longitudinally aligned. In another embodiment (not shown), the stud is an integral component of the end of the ultrasonic transducer. For example, the treaded stud and the velocity transformer may be of a single unit construction with the stud projecting from a distal surface of the velocity transformer at the distal end of the acoustic assembly. In this embodiment, the stud is not a separate component and does not require a recess in the end of the transducer.

Figure 3A:
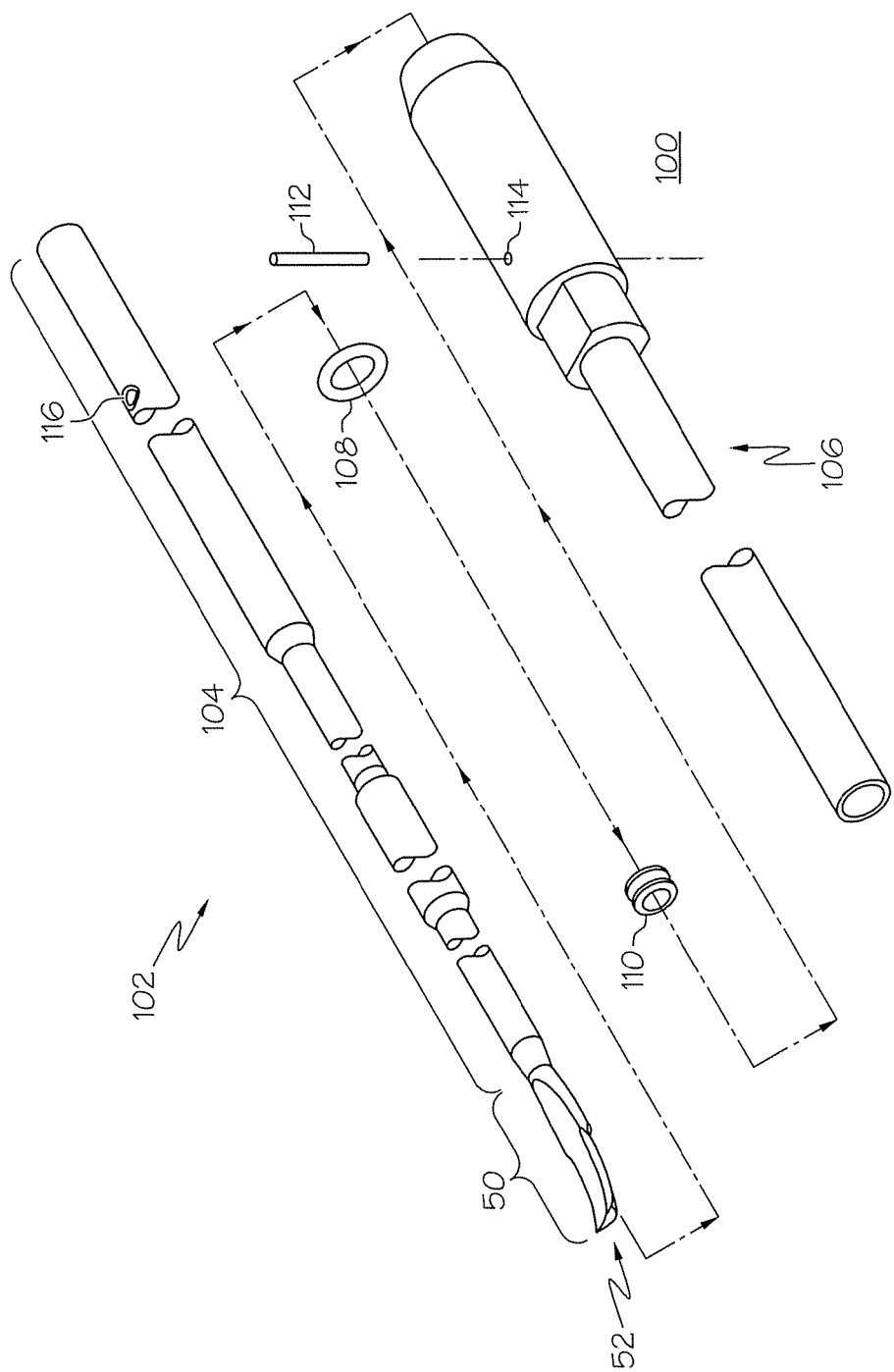
FIG. 3A illustrates an exploded perspective view of one embodiment of an ultrasonic surgical instrument comprising a single-element end effector that may be coupled to the ultrasonic system illustrated in FIG. 1.

FIG. 3A illustrates an exploded perspective view of one embodiment of ultrasonic surgical instrument 100 comprising a single-element end effector that may be coupled to handpiece assembly 60 (FIG. 1) of ultrasonic system 10. Ultrasonic surgical instrument 100 may be employed with the above-described ultrasonic system 10. However, as described herein, those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical end effector embodiments disclosed herein should not be limited to use only in connection with the exemplary ultrasonic surgical instrument described above.

In the embodiment illustrated in FIG. 3A, the elongated transmission component is shown as ultrasonic waveguide 104 and the end effector is shown as a single element end effector or blade 50 suitable to cut and/or coagulate tissue. The blade 50 may be symmetrical or asymmetrical.

The length of blade 50 may be substantially equal to an integral multiple of one-half system wavelengths ($n\lambda/2$). Distal end 52 of blade 50 may be disposed near an anti-node in order to provide the maximum longitudinal excursion of distal end 52. When the transducer assembly is energized, distal end 52 of the blade 50 may be configured to move in the range of, for example, approximately 10 to 500 microns peak-to-peak, and preferably in the range of about 30 to 150 microns at a predetermined vibrational frequency.

Blade 50 may be coupled to ultrasonic transmission waveguide 104. Blade 50 and ultrasonic transmission guide 104 as illustrated are formed as a single unit of construction from a material suitable for transmission of ultrasonic energy such as, for example, Ti6Al4V (an alloy of titanium including aluminum and vanadium), aluminum, stainless steel, other known materials, or combinations thereof. Alternately, blade 50 may be separable (and of differing composition) from ultrasonic transmission waveguide 104, and coupled by, for example, a stud, weld, glue, quick connect, or other suitable known methods. The length of ultrasonic transmission waveguide 104 may be substantially equal to an integral number of one-half system wavelengths ($n\lambda/2$), for example. Ultrasonic transmission waveguide 104 also may be preferably fabricated from a solid core shaft constructed out of material that propagates ultrasonic energy efficiently, such as titanium alloy (e.g., Ti6Al4V) or an aluminum alloy, for example. Ultrasonic transmission waveguide 104 also may be fabricated from a hollow core shaft constructed out of similar materials. Ultrasonic transmission waveguide 104 also may be fabricated with a combination solid/hollow core shaft, for example, a solid core shaft with hollow cavities positioned at various locations along the length of the shaft.

In the embodiment illustrated in FIG. 3A, ultrasonic transmission waveguide 104 is positioned in outer sheath 106 by mounting O-ring 108 and sealing ring 110. One or more additional dampers or support members (not shown) also may be included along ultrasonic transmission waveguide 104. Ultrasonic transmission waveguide 104 is affixed to outer sheath 106 by mounting pin 112 that passes through mounting holes 114 in outer sheath 106 and mounting hole 116 in ultrasonic transmission waveguide 104.

Ultrasonic transmission waveguide 104 comprises longitudinally projecting attachment post 54 at a proximal end to couple to surface 30 of ultrasonic transmission waveguide 104 by a threaded connection such as stud 48 (FIG. 2). Ultrasonic transmission waveguide 104 may comprise a plurality of stabilizing silicone rings or compliant supports (not shown) positioned at a plurality of nodes. The silicone rings dampen undesirable vibration and isolate the ultrasonic energy from outer sheath 106 assuring the flow of ultrasonic energy in a longitudinal direction to distal end 52 of blade 50 with maximum efficiency.

Outer sheath 106 generally includes a hub and an elongated tubular member. The tubular member is attached to the hub and has an opening extending longitudinally therethrough. Ultrasonic transmission waveguide 104 extends through the opening of the tubular member and attaches to the distal end of transducer 14. As previously discussed, outer sheath 106 attaches to ultrasonic transmission waveguide 104 by mounting pin 112 passed through mounting holes 114. Outer sheath 106 may be attached to a distal end of housing 16 or an adapter attached to housing 16 such that the rear hub of outer sheath 106 is supported by housing 106 when excessive bending torque is applied during surgery. Silicone rings isolate ultrasonic transmission waveguide 104 from outer sheath 106.

The adapter of the sheath is preferably constructed from plastic, and the tubular member is fabricated from stainless steel. Alternatively, ultrasonic transmission waveguide 104 may have polymeric material surrounding it to isolate it from outside contact.

The distal end of ultrasonic transmission waveguide 104 may be coupled to the proximal end of blade 50 by an internal threaded connection, preferably at or near an anti-node. It is contemplated that blade 50 may be attached to ultrasonic transmission waveguide 104 by any suitable means, such as a welded joint or the like. Although blade 50 may be detachable from ultrasonic transmission waveguide 104, it is also contemplated that blade 50 and ultrasonic transmission waveguide 104 may be formed as a single unitary piece.

Ultrasonic surgical instrument 100 may be sterilized by methods known in the art such as, for example, gamma radiation sterilization, ethylene oxide processes, autoclaving, soaking in sterilization liquid, or other known processes. In the illustrated embodiment, ultrasonic transmission assembly 102 includes an ultrasonic end effector, generally designated as the ultrasonic blade 50, and ultrasonic transmission waveguide 104. Blade 50 and ultrasonic transmission waveguide 104 are illustrated as a single unit construction from a material suitable for transmission of ultrasonic energy such as, for example, Ti6Al4V, aluminum, stainless steel, other known materials, and combinations thereof. Alternately, ultrasonic blade 50 may be separable (and of differing composition) from ultrasonic transmission waveguide 104, and coupled by, for example, a stud, weld, glue, quick connect, or other known methods. Ultrasonic transmission waveguide 104 may have a length substantially equal to an integral number of one-half system wavelengths (nλ/2), for example.

Figure 3D:
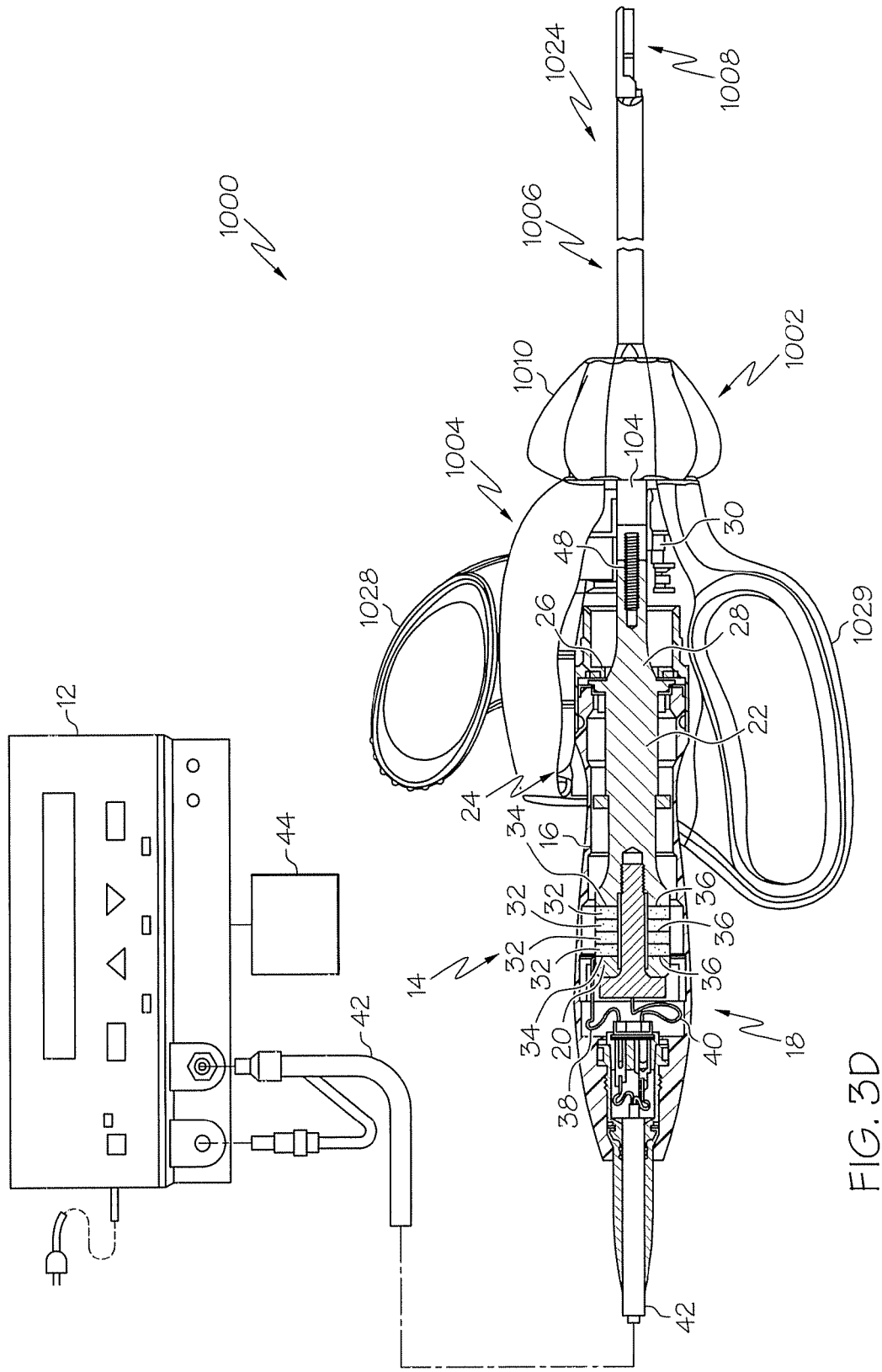
FIG. 3D illustrates one embodiment of an ultrasonic system comprising one embodiment of a multiple element end effector as shown in FIGS. 3B and 3C.

FIG. 3B illustrates one embodiment of ultrasonic surgical instrument 1002 comprising a multiple-element end effector as shown in FIG. 3A. FIG. 3C illustrates a perspective view of one embodiment of the multiple-element end effector as shown in FIG. 3B. With reference to FIGS. 3B, 3C and 3D, clamped coagulating shears 1002 may be preferably attached to and removed from acoustic assembly 18 as a unit. The proximal end of clamped coagulating shears 1002 preferably acoustically couples to distal surface 30 of acoustic assembly 18. Clamped coagulating shears 1002 may be coupled to acoustic assembly 18 by any suitable means.

Clamped coagulating shears 1002 preferably includes instrument housing 1004 and elongated member 1006. Elongated member 1006 may be selectively rotated with respect to instrument housing 1004. Instrument housing 1004 includes pivoting handle portion 1028 and fixed handle portion 1029.

An indexing mechanism (not shown) is disposed within a cavity of instrument housing 1004. The indexing mechanism is preferably coupled or attached on inner tube 1014 to translate movement of pivoting handle portion 1028 to linear motion of inner tube 1014 to open and close multi-element end assembly 1008. When pivoting handle portion 1028 is moved toward fixed handle portion 1029, the indexing mechanism slide inner tube 1014 rearward to pivot multi-element end assembly 1008 into a closed position. The movement of pivoting handle portion 1028 in the opposite direction slides the indexing mechanism to displace inner tube 1014 in the opposite direction, i.e., forwardly, and hence pivot multi-element end assembly 1008 into its open position in the direction indicated by arrow 1020 as shown in FIG. 3B.

Pivoting handle portion 1028 includes thumb loop 1030. Pivot pin 1032 is disposed through a first hole of pivoting handle portion 1028 to allow pivoting as shown by arrow 1034 in FIG. 3B. As thumb loop 1030 of pivoting handle portion 1028 is moved in the direction of arrow 1034, away from instrument housing 1004, inner tube 1014 slides rearward to pivot multi-element end assembly 1008 into a closed position.

Elongated member 1006 of clamped coagulating shears 1002 extends from instrument housing 1004. Elongated member 1006 preferably includes an outer member or outer tube 1012, an inner member or inner tube 1014, and a transmission component or ultrasonic transmission waveguide 104.

The multiple-element end effector or multi-element end assembly 1008 includes clamp arm 1018, tissue pad 1036, and ultrasonic blade 1016. Clamp arm 1018 is pivotally mounted about a pivot pin (not shown) to rotate in the direction indicated by arrow 1038. Ultrasonic blade 1016 comprises tapered concave surface 1040 extending inwardly into the blade body.

FIG. 3D illustrates one embodiment of ultrasonic system 1000 comprising one embodiment of a multiple-element end effector. One embodiment of ultrasonic system 1000 comprises ultrasonic generator 12 coupled to ultrasonic transducer 14, described with reference to FIG. 1. Ultrasonic transducer 14 is coupled to clamped coagulating shears 1002 comprising instrument housing 1004. Acoustic assembly 18 delivers energy to multi-element end assembly 1008. In order for acoustic assembly 18 to deliver energy to multi-element end assembly 1008, all components of acoustic assembly 18 must be acoustically coupled to the ultrasonically active portions of clamped coagulating shears 1002. Accordingly, the distal end of ultrasonic transducer 14 may be acoustically coupled at surface 30 to the proximal end of ultrasonic transmission waveguide 104 by threaded connection stud 48.

As previously discussed with reference to ultrasonic system 10 (FIG. 1), the components of acoustic assembly 18 are preferably acoustically tuned such that the length of any assembly is an integral number of one-half wavelengths (nλ/2), where the wavelength λ is the wavelength of a pre-selected or operating longitudinal vibration drive frequency $f_d$ of acoustic assembly 18, and where n is any positive integer. Acoustic assembly 18 may incorporate any suitable arrangement of acoustic elements.

Ultrasonic surgical instrument 100 and clamped coagulating shears 1002 may be sterilized by methods known in the art such as, for example, gamma radiation sterilization, ethylene oxide processes, autoclaving, soaking in sterilization liquid, or other known processes. In the embodiment illustrated in FIGS. 1 and 2, ultrasonic transmission assembly 102 of surgical instrument 100 includes the single element ultrasonically actuated end effector or blade 50 coupled to ultrasonic transmission waveguide 104. Blade 50 and ultrasonic transmission waveguide 104 are illustrated as a single unit construction from a material suitable for transmission of ultrasonic energy as previously discussed (e.g., Ti6Al4V, Aluminum, Stainless Steel, or other known materials). Alternately, blade 50 may be separable (and of differing composition) from ultrasonic transmission waveguide 104, and coupled by, for example, a stud, weld, glue, quick connect, or other known methods.

In the embodiment illustrated in FIGS. 3B and 3D, ultrasonic transmission assembly 1024 of clamped coagulating shears 1002 includes multi-element end assembly 1008 coupled to ultrasonic transmission waveguide 104. The length of ultrasonic transmission waveguide 104 may be substantially equal to an integral number of one-half system wavelengths (nλ/2), for example. Ultrasonic transmission waveguide 104 may be preferably fabricated from a solid core shaft constructed out of material that propagates ultrasonic energy efficiently, such as titanium alloy (i.e., Ti6Al4V) or an aluminum alloy, for example.

FIG. 4 is a perspective view of one embodiment of a multiple-element end effector 1111 comprising clamp arm assembly 1108 and ultrasonic blade 1116. Clamp arm assembly 1108 includes clamp arm 1118 and tissue pad 1136. End effector 1111 is positioned on the distal end of outer tube 1112.

The active length of an ultrasonic instrument is the length of the end effector from the distal end that achieves desired tissue effects (e.g., cutting and coagulation) during use. The active length of an ultrasonic instrument may be defined as the length/distance from the distal end of the end effector (where the ultrasonic displacement is maximum) to where ultrasonic displacement decreases below a predetermined level in the proximal direction. Outside the active length, the end effector may not deliver sufficient heat to tissue in contact with the end effector to achieve efficient and/or effective cutting and/or coagulation, for example.

In some instances, the active length is defined as the length from the distal end of the end effector to the proximal location where the ultrasonic displacement decreases to 50% of the maximum displacement. The 50% standard takes account of the ultrasonic energy generally necessary to achieve acceptable cutting and/or coagulation. However, other percentage decreases in ultrasonic displacement may be used to quantitatively define the active length (and the nodal gap). Those of ordinary skill in the art can quantitatively define the active length (and the nodal gap) according to the specific ultrasonic system involved.

Figure 5:
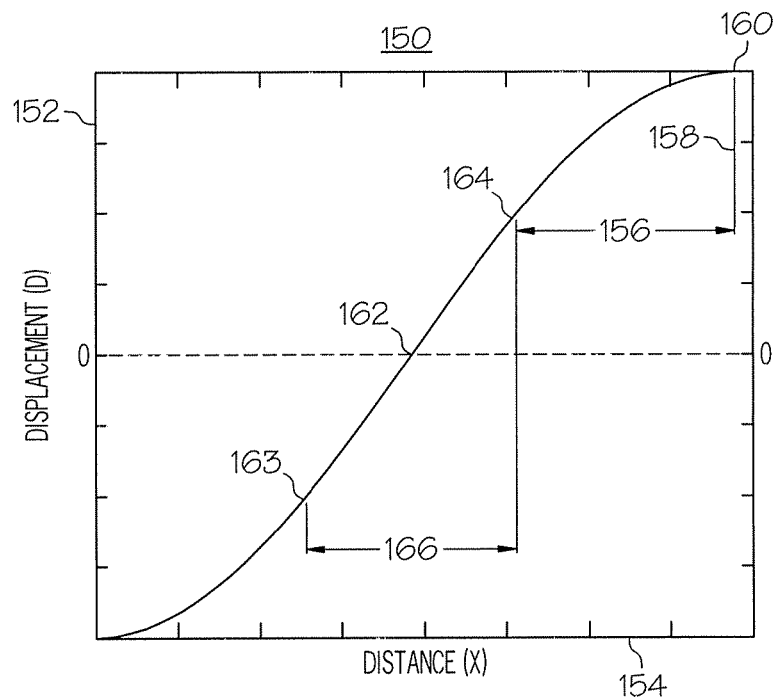
FIG. 5 is a graph of ultrasonic displacement as a function of length/distance in one embodiment of an end effector.

FIG. 5 is a graph 150 of ultrasonic displacement 152 as a function of length/distance 154 for one-half of a wavelength (λ/2) of the longitudinal ultrasonic vibration in one embodiment of an end effector. Active length 156 is the length from distal end 158 of the end effector where maximum displacement 160 occurs to point 164 where displacement has decreased to 50% of the maximum 160. Generally, active length 156 is a fraction of a quarter wavelength (λ/4). The length of the end effector may be substantially equal to an integral multiple of one-half system wavelengths (nλ/2), where "n" is any positive integer. Therefore, active length 156 is an even smaller fraction of the overall length of the end effector (not shown). Nodal gap 166 corresponds to the length segment of the end effector centered at node 162 and extending between point 164 and point 163. Sufficient ultrasonic energy may not be imparted to the tissue in the nodal gap region (adjacent to nodal gap 166 along the length of an end effector) to achieve acceptable cutting and/or coagulation. If nodal gap 166 can be bridged, filled or otherwise eliminated, then active length 156 may increase substantially.

Figure 6:
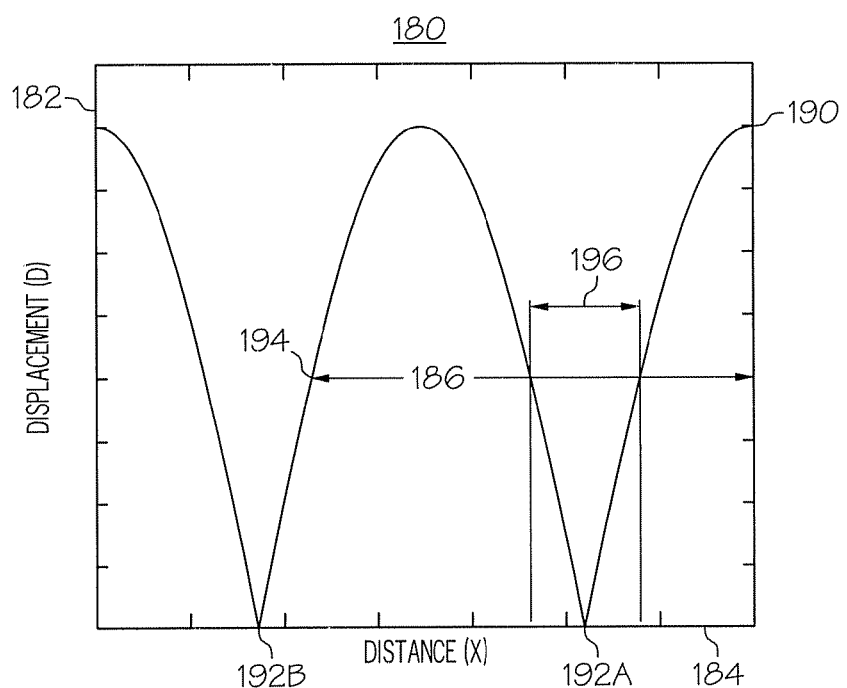
FIG. 6 is a graph of rectified ultrasonic displacement as a function of length/distance in one embodiment of an end effector.

FIG. 6 is a graph 180 of rectified ultrasonic displacement 182 as a function of length/distance 184 for a full wavelength (λ) of the longitudinal ultrasonic vibration in one embodiment of an end effector. If nodal gap 196 is bridged, filled or otherwise eliminated, then the active length is substantially increased to potential active length 186. If nodal gap 196 is bridged, filled or otherwise eliminated, potential active length 186 extends from point 190 of maximum ultrasonic displacement at the distal end of an end effector, past first node 192A and corresponding nodal gap 196, to point 194 where ultrasonic displacement has decreased to 50% of the maximum approaching second node 192B proximal to the distal end and first node 192A.

The various embodiments relate, in general, to methods developed to bridge, fill or otherwise eliminate the nodal gap. The various embodiments relate, more specifically, to end effectors for use with ultrasonic surgical instruments that embody the methods to bridge, fill or otherwise eliminate the nodal gap. A first method is to narrow or close the nodal gap by modifying the composition of an end effector. This method may effectively bridge the nodal gap. A second method is to fill the nodal gap by delivering heat to tissue in the nodal gap region.

By definition, the ultrasonic displacement at a node is zero. As illustrated in FIG. 6, the displacement increases in magnitude in an approximately linear fashion in the vicinity of the node. If the slope of the rectified displacement versus distance curve (displacement-distance curve) were increased in the vicinity of the node, then the nodal gap would decrease. In the limit as the slope approached infinity (i.e., vertical), the nodal gap would go to zero. To increase the displacement in the vicinity of the node, and therefore, to decrease the nodal gap, a segment of material having a relatively lower specific acoustic impedance value than the material comprising the main portion of an end effector can be inserted in the end effector along a longitudinal axis of the end effector. The relative steepness of the slope of the displacement-distance curve in the vicinity of the node can be determined by the ratio of the specific acoustic impedance values of the main portion of the end effector to the segment located at or near the node.

Characteristic acoustic impedance is the ratio of effective sound pressure at a point to the particle velocity at that point in a free, progressive wave in a medium. Characteristic acoustic impedance is equal to the product of the density of the medium and the speed of sound in the medium and is an intrinsic material property. The specific acoustic impedance of a system is the product of the characteristic acoustic impedance of the material comprising the system and the cross-sectional area of the system through which a wave progresses. Therefore, the displacement in the vicinity of the node, and thus the slope of the displacement-distance curve in the vicinity of the node can be increased by differences in material properties, differences in cross-sectional area, or a combination of both.

Figure 7:
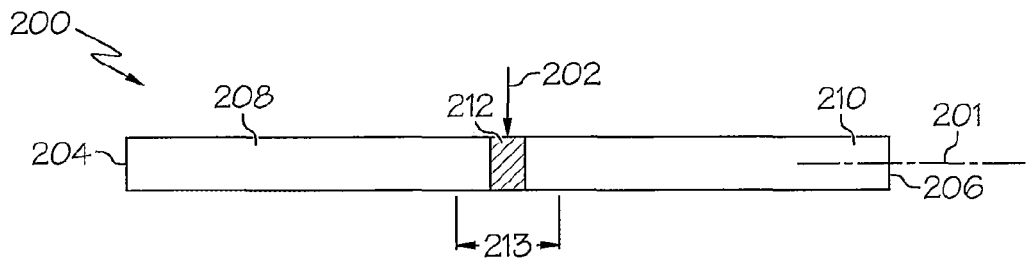
Figure 8A:
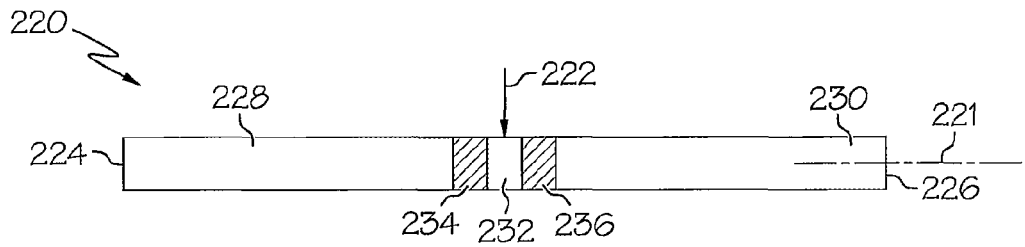
FIG. 8A is a side view of one embodiment of a single-element end effector comprising three insert segments.
Figure 8B:
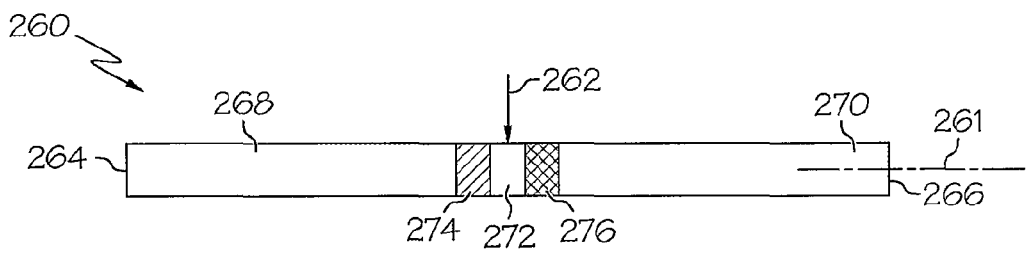
FIG. 8B is a side view of one embodiment of a single-element end effector comprising a proximal end and a distal end and extending along a longitudinal axis.
Figure 8C:
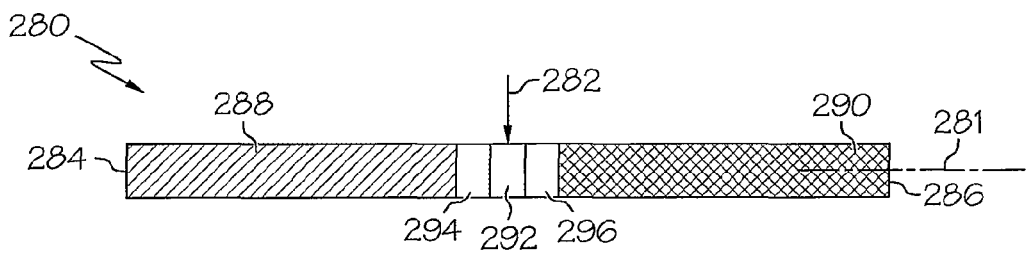
FIG. 8C is a side view of one embodiment of a single-element end effector comprising a proximal end and a distal end and extending along a longitudinal axis.
Figure 9:
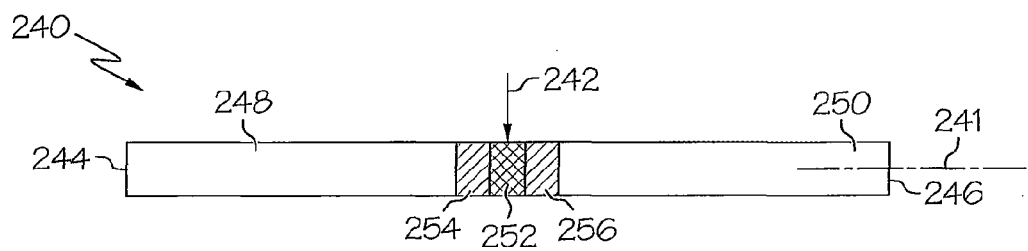

FIGS. 7-9 illustrate various embodiments of an end effector comprising insert segments having different specific acoustic impedance values than the main portion of the end effector. FIG. 7 is a side view of one embodiment of single-element end effector 200 comprising one insert segment 212. End effector 200 comprises proximal end 204 and distal end 206 and extends along longitudinal axis 201. Insert segment 212 is located between proximal end segment 208 and distal end segment 210 along longitudinal axis 201 of end effector 200. In one embodiment, insert segment 212 may be located at or near node 202 and positioned within nodal gap 213. In another embodiment, insert segment 212 may be located within nodal gap 213 but offset from node 202 (not shown). In yet another embodiment, the length of insert segment 212 along longitudinal axis 201 may correspond to the length of nodal gap 213. In still another embodiment, insert segment 212 may be offset from node 202 and completely or partially outside nodal gap 213.

In various embodiments, proximal end segment 208 and distal end segment 210 comprise a first portion or main portion of end effector 200 having a first specific acoustic impedance value. Insert segment 212 comprises a second portion having a second specific acoustic impedance value different than the first specific acoustic impedance value. Insert segment 212 may comprise a coating on end effector 200 of a material having a second specific acoustic impedance value. The difference between the first specific acoustic impedance value and the second specific acoustic impedance value may be a consequence of differences in material properties between the first portion and the second portion, or differences in cross-sectional area between the first portion and the second portion, or both. In various embodiments, the second acoustic impedance value is less than the first specific acoustic impedance value due to the second portion comprising a material having a relatively lower characteristic acoustic impedance value and the first portion comprising a material with a relatively higher characteristic acoustic impedance value. In various embodiments, the second acoustic impedance value is less than the first specific acoustic impedance value due to the second portion having a smaller cross-sectional area than the first portion. In various embodiments, the reduction in cross-sectional area is due to internal bores or cavities that have been bored into end effector 200 (see FIG. 26A-C).

Distal end segment 210, proximal end segment 208 and insert segment 212 may comprise matching cross-sectional areas. Distal end segment 210 and proximal end segment 208 may comprise a first material and insert segment 212 may comprise a second material having a lower characteristic acoustic impedance value than the first material. Alternatively, distal end segment 210, proximal end segment 208 and insert segment 212 all may comprise the same material, but insert segment 212 may have a smaller cross-sectional area than distal end segment 210 and proximal end segment 208. However, the cross-sectional area of insert segment 212 can only be decreased to a value that will safely support the internal ultrasonic stresses that maximize at node 202. Decreased cross-sectional area results in decreased specific acoustic impedance, which results in increased ultrasonic displacement in the nodal gap 213, whereby the nodal gap 213 is narrowed. In various embodiments, the reduction in the cross-sectional area of insert segment 212 is due to internal bores or cavities formed in end effector 200 (see FIGS. 26A-C).

In various embodiments, insert segment 212 is comprised of an acoustically lossy material. As used herein, a lossy material is one that dissipates as heat acoustic energy passing through the material. Generally, end effectors and other components of ultrasonic instruments are not comprised of lossy materials because it is desirable to efficiently transmit ultrasonic vibrational energy to the end effector with minimal energy dissipation. The ultrasonic displacement of the end effector converts the ultrasonic vibrational energy into heat energy during the interaction with tissue. However, due to minimal ultrasonic displacement, the end effector may not effectively or efficiently convert ultrasonic vibrational energy to heat energy in the nodal gap. Therefore, the insertion of a lossy material in an end effector at or near the nodal gap would result in the conversion of ultrasonic energy to heat in the nodal gap due to internal energy losses from the lossy material. Specifically, the lossy material allows internal ultrasonic stresses that are at a maximum at a node in the material to dissipate as heat energy. The heat losses from the lossy segment are conducted to the tissue, effectively filling the nodal energy gap in the nodal gap region.

In various embodiments, insert segment 212 comprises a lossy material and thus could potentially continue to generate heat when an ultrasonic instrument comprising an end effector 200 is operated in air or other media and not in contact with tissue. The continually generated heat could increase the localized temperature in nodal gap 213 of end effector 200. The temperature rise could be mitigated by heat transfer to neighboring regions of end effector 200. Accordingly, to mitigate the rise in temperature, in various embodiments insert segment 212 may be formed with lossy material having a cross-sectional area that is less than the cross-sectional area of distal end segment 210 and proximal end segment 208. Reducing the amount of material (i.e., decreasing the cross-sectional area of end effector 200) in nodal gap 213 decreases the specific acoustic impedance value and therefore narrows and simultaneously fills the nodal gap 213. In various embodiments, insert segment 212 comprises a material that is lossy and has a reduced cross sectional area. In various embodiments, the reduction in the cross-sectional area of insert segment 212 is due to internal bores or cavities formed in end effector 200 (see FIGS. 26A-C). In various embodiments, insert segment 212 comprises a coating of a lossy material localized in a portion or region on end effector 200. In various embodiments, insert segment 212 comprises a coating of a high friction material localized in a portion or region on end effector 200. A high friction material has a coefficient of friction greater than the coefficient of friction of the material comprising the main portion of end effector 200.

The magnitude of the narrowing of nodal gap 213 is directly dependant on the relative values of the specific acoustic impedance values of insert segment 212 and of distal end segment 210 and proximal end segment 208. The relative steepness of the slope of the displacement-distance curve in the vicinity of node 202 can be determined by the ratio of the specific acoustic impedance value of distal end segment 210 to the specific acoustic impedance value of insert segment 212. To substantially narrow nodal gap 213 by employing materials having different characteristic acoustic impedance values, it may require that the materials have characteristic acoustic impedance values that are substantially different. This may require an end effector formed mostly of materials comprising a relatively high characteristic acoustic impedance value.

FIG. 8A is a side view of one embodiment of a single-element end effector 220 comprising insert segments 232, 234 and 236. In various embodiments, insert segments 232, 234 and 236 may be located between proximal end segment 228 and distal end segment 230 at or near node 222. Proximal end segment 228 and distal end segment 230 collectively comprise the main portion of end effector 220. Insert segment 232 is formed of a material having a higher characteristic acoustic impedance value than the material forming the main portion of end effector 220 and is located between two additional insert segments 234 and 236 formed of a material having a lower characteristic acoustic impedance value than the material forming the main portion of end effector 220. The material forming insert segment 232 comprises self-heating properties due mainly to its higher characteristic impedance value. Therefore, positioning insert segment 232 with self heating properties in an intermediate position at or near the node 222 may effectively minimize or substantially eliminate the nodal gap. In this context, the intermediate insert segment 232 having the greatest characteristic acoustic impedance value functions in a manner similar to an acoustically lossy insert segment as described above.

End effector 220 comprises a proximal end 224 and a distal end 226 and extends along a longitudinal axis 221. Intermediate insert segment 232 is located between proximal insert segment 234 and distal insert segment 236 along longitudinal axis 221. Proximal insert segment 234, intermediate insert segment 232 and the distal insert segment 236 are located between proximal end segment 228 and distal end segment 230 along longitudinal axis 221. Distal end segment 230 comprises a first acoustic impedance material, distal insert segment 236 comprises a second acoustic impedance material, intermediate insert segment 232 comprises a third acoustic impedance material, proximal insert segment 234 comprises a fourth acoustic impedance material, and proximal end segment 228 comprises a fifth acoustic impedance material.

In one embodiment, the second acoustic impedance material (of distal insert segment 236) and the fourth acoustic impedance material (of proximal insert segment 234) are the same material. In one embodiment, the first acoustic impedance material (of distal end segment 230) and the fifth acoustic impedance material (of proximal end segment 228) are the same material. In one embodiment, the first acoustic impedance material (of distal end segment 230), the third acoustic impedance material (of intermediate insert segment 232) and the fifth acoustic impedance material (of proximal end segment 228) are the same material. In one embodiment, the first acoustic impedance material, the third acoustic impedance material and the fifth acoustic impedance material each have greater characteristic acoustic impedance values than the second acoustic impedance material and the fourth acoustic impedance material. In one embodiment, all five acoustic impedance materials have different specific acoustic impedance values.

In one embodiment, intermediate insert segment 232 may be located at or near node 222 and positioned within the nodal gap. In another embodiment, intermediate insert segment 232 may be located within the nodal gap but offset from node 222 (not shown). In yet another embodiment, the length of insert segment 232 along longitudinal axis 221 may correspond to the length of the nodal gap (not shown). In still another embodiment, intermediate insert segment 232 may be offset from node 222 and completely or partially outside the nodal gap (not shown). In yet another embodiment, proximal insert segment 234, intermediate insert segment 232 and distal insert segment 236 may be located within the nodal gap. In still another embodiment, proximal insert segment 234, intermediate insert segment 232 and distal insert segment 236 may be located partially or completely outside the nodal gap.

FIG. 8B is a side view of one embodiment of a single-element end effector 260 comprising a proximal end 264 and a distal end 266 and extending along a longitudinal axis 261. Intermediate insert segment 272 is located between proximal insert segment 274 and distal insert segment 276 along longitudinal axis 261. Proximal insert segment 274, intermediate insert segment 272 and the distal insert segment 276 are located between proximal end segment 268 and distal end segment 270 along longitudinal axis 261. Distal end segment 270 comprises a first acoustic impedance material, distal insert segment 276 comprises a second acoustic impedance material, intermediate insert segment 272 comprises a third acoustic impedance material, proximal insert segment 274 comprises a forth acoustic impedance material, and proximal end segment 268 comprises a fifth acoustic impedance material.

In various embodiments, the second acoustic impedance material (or distal insert segment 276) and the fourth acoustic impedance material (of proximal insert segment 274) are different materials.

FIG. 8C is a side view of one embodiment of a single-element end effector 280 comprising a proximal end 284 and a distal end 286 and extending along a longitudinal axis 281. Intermediate insert segment 292 is located between proximal insert segment 294 and distal insert segment 296 along longitudinal axis 281. Proximal insert segment 294, intermediate insert segment 292 and the distal insert segment 296 are located between proximal end segment 288 and distal end segment 290 along longitudinal axis 281. Distal end segment 290 comprises a first acoustic impedance material, distal insert segment 296 comprises a second acoustic impedance material, intermediate insert segment 292 comprises a third acoustic impedance material, proximal insert segment 294 comprises a forth acoustic impedance material, and proximal end segment 268 comprises a fifth acoustic impedance material.

In various embodiments, the first acoustic impedance material (of the distal end segment 290) and the fifth acoustic impedance material (of proximal end segment 288) are different materials.

FIG. 9 is a side view of one embodiment of a single element end effector 240 comprising insert segments 252, 254 and 256. End effector 240 comprises proximal end 244 and distal end 246 and extends along longitudinal axis 241. Intermediate insert segment 252 is located between proximal insert segment 254 and distal insert segment 256 along longitudinal axis 241. Proximal insert segment 254, intermediate insert segment 252 and distal insert segment 256 are located between proximal end segment 248 and distal end segment 250 along longitudinal axis 241. Distal end segment 250 comprises a first acoustic impedance material, distal insert segment 256 comprises a second acoustic impedance material, intermediate insert segment 252 comprises a third acoustic impedance material, proximal insert segment 254 comprises a fourth acoustic impedance material, and proximal end segment 248 comprises a fifth acoustic impedance material.

In various embodiments, the third acoustic impedance material (of intermediate insert segment 252) may have a greater acoustic impedance value than the first acoustic impedance material (of distal end segment 250) and the fifth acoustic impedance material (of proximal end segment 248). The second acoustic impedance material (of distal insert segment 256) and the fourth acoustic impedance material (of proximal insert segment 254) may have lower acoustic impedance values than the first acoustic impedance material and the fifth acoustic impedance material.

In one embodiment, intermediate insert segment 252 may be located at or near node 242 and positioned within the nodal gap. In another embodiment, intermediate insert segment 252 may be located within the nodal gap but offset from node 242 (not shown). In yet another embodiment, the length of insert segment 252 along longitudinal axis 241 may correspond to the length of the nodal gap (not shown). In still another embodiment, intermediate insert segment 252 may be offset from node 242 and completely or partially outside the nodal gap (not shown). In yet another embodiment, proximal insert segment 254, intermediate insert segment 252 and distal insert segment 256 may be located within the nodal gap. In still another embodiment, proximal insert segment 254, intermediate insert segment 252 and distal insert segment 256 may be located partially or completely outside the nodal gap.

The insert segments described in conjunction with FIGS. 7-9 have been generally described in terms of segments comprising materials having various acoustic impedance values and acoustically lossy materials. However, the insert segments described above encompass regions of the single-element end effectors having coatings of materials having various acoustic impedance values, coatings of acoustically lossy materials and coatings of high friction materials. Moreover, the insert segments having different acoustic impedance values can be formed by cold working various regions of single-element end effectors comprising single materials, for example. The present invention is not limited in this context.

The characteristic acoustic impedances of three common metals in surgical instruments are substantially different.

Figure 10:
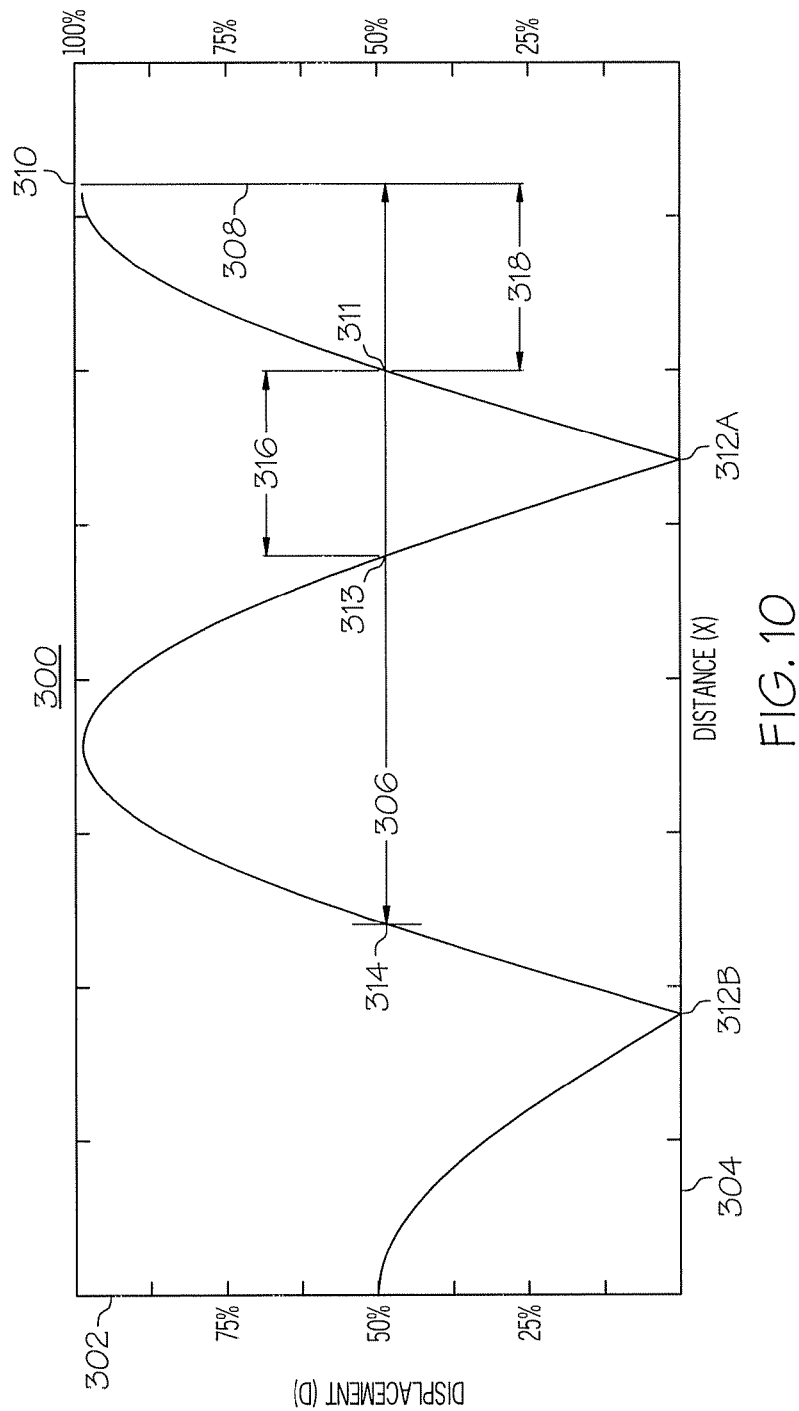
FIGS. 10-12 are graphs of rectified ultrasonic displacement as a function of length/distance of various embodiments of stainless steel end effectors, where.

Stainless Steel (SS): $40*10^6$ rayls
Titanium (TI): $22*10^6$ rayls
Aluminum (AL): $14*10^6$ rayls TABLE 1 presents the results of a mathematical model based on a simple end effector design using the materials listed above and various configurations for bridging and/or filling the nodal gap. The end effectors comprise a main portion or first portion comprising a proximal end segment and a distal end segment, and further comprise a second portion comprising an insert segment. The length and position of the insert segment may be selected so that the insert segment is located at the node and the slopes of the displacement-distance curves intersect at a predetermined displacement value as illustrated in FIGS. 10-12. Lengths are reported in inches (mm) and the cross-sectional areas of the insert segments are reported as a percentage of the cross-sectional areas of the main portions of the end effectors.

TABLE 1

Nodal Gap and Active Length for Bridged/Filled End Effectors.

| Material Configuration | Insert Segment Area | Nodal Gap | Standard Active Length | Potential Active Length |
|---|---|---|---|---|
| SS | — | 0.601 (15.3) | 0.600 (15.2) | 2.401 (61.0) |
| SS-AL-SS | 100% | 0.221 (5.61) | 0.597 (15.2) | 2.020 (51.3) |
| SS-AL-SS | 50% | 0.134 (3.40) | 0.600 (15.2) | 1.934 (49.1) |
| TI | — | 0.579 (14.7) | 0.578 (14.7) | 2.313 (58.8) |
| TI-AL-TI | 100% | 0.411 (10.4) | 0.579 (14.7) | 1.934 (49.1) |
| TI-AL-TI | 50% | 0.209 (5.31) | 0.576 (14.6) | 1.939 (49.3) |

TABLE 1-continued

Nodal Gap and Active Length for Bridged/Filled End Effectors.

| Material Configuration | Insert Segment Area | Nodal Gap | Standard Active Length | Potential Active Length |
|---|---|---|---|---|
| TI-TI-TI | 50% | 0.319 (8.10) | 0.583 (14.8) | 2.074 (52.7) |
| AL | — | 0.592 (15.0) | 0.591 (15.0) | 2.365 (60.1) |
| AL-AL-AL | 50% | 0.329 (8.28) | 0.588 (14.9) | 2.086 (53.0) |

The most substantial reduction in the nodal gap is seen with the stainless steel end effector comprising aluminum inserts. The stainless steel end effector with no insert has a nodal gap of 0.601 inches measured between the 50% ultrasonic displacement amplitude points. The stainless steel end effector comprising an aluminum insert segment having a cross-sectional area matching the cross-sectional area of the stainless steel portion has a nodal gap narrowed to 0.221 inches measured between the 50% ultrasonic displacement amplitude points. The stainless steel end effector comprising an aluminum insert segment having a cross-sectional area half the cross-sectional area of the stainless steel portion has a nodal gap narrowed to 0.134 inches measured between the 50% ultrasonic displacement amplitude points. This is a 78 percent reduction in the length of the nodal gap.

FIGS. 10-12 are graphs of rectified ultrasonic displacement as a function of length/distance (displacement-distance curves) of various embodiments of stainless steel end effectors similar to those previously described. FIG. 10 is a graph 300 of rectified ultrasonic displacement 302 as a function of length/distance 304 for an end effector formed entirely of stainless steel. Standard active length 318 is measured from distal end 308 of the end effector (where displacement is maximized at point 310) to the 50% ultrasonic displacement point 311 distal to node 312A. Nodal gap 316 extends between the 50% ultrasonic displacement points 311 and 313 on either side of node 312A. Potential active length 306 extends from distal end 308 to the 50% ultrasonic displacement point 314 distal to node 312B.

FIG. 11 is a graph 320 of rectified ultrasonic displacement 322 as a function of length/distance 324 for a stainless steel end effector comprising an aluminum insert segment having a cross-sectional area matching the cross-sectional area of the stainless steel portion. Standard active length 338 is measured from distal end 328 of the end effector to the 50% ultrasonic displacement point 331 distal to node 332A. Nodal gap 336 extends between the 50% ultrasonic displacement points 331 and 333 on either side of node 332A. Potential active length 326 extends from the distal end 328 to the 50% ultrasonic displacement point 334 distal to node 332B. Comparing nodal gap 316 in FIG. 10 and nodal gap 336 in FIG. 11, it may be observed that the addition of the aluminum insert segment to the stainless steel end effector may substantially narrow the nodal gap.

FIG. 12 is a graph 340 of rectified ultrasonic displacement 342 as a function of length/distance 344 for a stainless steel end effector comprising an aluminum insert segment having a cross-sectional area half the cross-sectional area of the stainless steel portion. Standard active length 358 is measured from distal end 348 of the end effector to the 50% ultrasonic displacement point 351 distal to node 352A. Nodal gap 356 extends between the 50% ultrasonic displacement points 351 and 353 on either side of node 352A. Potential active length 346 extends from distal end 348 to the 50% ultrasonic displacement point 354 distal to node 352B. Comparing nodal gap 316 in FIG. 10, nodal gap 336 in FIG. 11, and nodal gap 356 in FIG. 12, it may be observed that the addition of the aluminum insert segment to the stainless steel end effector, where the cross-sectional area of the aluminum insert segment is half of the cross-sectional area of the stainless steel main portion of the end effector, may further substantially narrow the nodal gap.

Those of ordinary skill in the art will recognize that the particular configuration of an end effector (i.e., the dimensions, shape, and exact materials of construction) is determined, in part, by the particular characteristics of the ultrasonic instrument in which the end effector is to be used. However, the end effectors described herein may include, but are not limited to, ultrasonic surgical blade designs such as those described in conjunction with reference to FIGS. 1-4, or any other known surgical implement suitable for use in an ultrasonic instrument.

The end effectors described herein may be manufactured using any known methods of machining or other suitable fabrication methods. For example, the TI-TI-TI or AL-AL-AL end effectors in Table 1 can readily be manufactured using standard lathe techniques and/or electrical discharge machining (EDM) techniques. Those of ordinary skill in the art will appreciate the details regarding the particular machining techniques employed, for example, the formation of recast layers during EDM that typically require buffing to prevent the metal from embrittling. In addition, end effectors comprising insert segments of dissimilar materials compared to the material of the main portion (e.g., the SS-AL-SS and TI-AL-TI configurations in Table 1) may be manufactured by any suitable methods, such as, for example, laser welding.

Those skilled in the art will also recognize that the shape and configuration of a reduced-area segment will be governed, in part, by the particular characteristics of the end effector and the ultrasonic system employed. It is also recognized that the term "insert segment" has been used herein to describe, among other things, a portion of an end effector that has a reduced cross-sectional area with respect to the main portion of the end effector. For example, "insert segment" may refer to a region of an end effector comprising an internal cavity or bore. The term "insert segment" has also been used herein to describe regions or portions of end effectors comprising coatings. The term "insert segment" is intended to describe these regions or portions of an end effector in a general manner and is not limiting with regard to the method by which the region or portion is manufactured.

Various embodiments have been described for bridging, filling or otherwise eliminating the nodal gap (e.g., narrowing the length of the nodal gap or filling the nodal energy gap with heat) by manipulating the materials and/or geometry of an end effector. Additional embodiments relate to filling the nodal energy gap with heat generated from structures interacting with an end effector. In these embodiments, the end effector may be an ultrasonic surgical blade that conducts heat generated due to frictional interaction with insert segments located on clamp arms and/or pads located on additional components of ultrasonic instruments. The insert segments and/or pads are positioned such that the frictionally-generated heat is conducted into the nodal gap region of the ultrasonic blade, effectively filling the nodal energy gap.

FIGS. 13-18 illustrate various embodiments of an ultrasonic surgical instrument. FIG. 13 is a partial side view of one embodiment of ultrasonic surgical instrument 400 in a conventional configuration without a tissue pad insert segment. Ultrasonic surgical instrument 400 comprises outer tube 418. Ultrasonic surgical blade 402 extends along longitudinal axis 422 coupled to the transducer, and has body 404 having proximal end 406 and distal end 408. Distal end 408 is moveable relative to longitudinal axis 422 by the vibrations produced by the transducer. Ultrasonic surgical instrument 400 further comprises non-vibrating clamp arm assembly 410 having proximal end 412 and distal end 414. Clamp arm assembly 410 further comprises tissue pad 416. Ultrasonic surgical blade 402 is positioned such that a length equal to approximately one-quarter of a wavelength (λ/4) of the ultrasonic vibrational wave is exposed corresponding to the active length of blade 402. Clamp arm 410 pivots near or at node 420. Clamp arm 410 is pivotally moveable from an open position to a closed position.

FIG. 14 is a partial side view of one embodiment of ultrasonic surgical instrument 450 having an insert segment 468 positioned in the tissue pad of clamp arm assembly 460. The ultrasonic surgical instrument 450 comprises an outer tube 472. Ultrasonic surgical instrument 450 is coupled to transducer 14 (FIG. 1) configured to produce vibrations along longitudinal axis 476 at a predetermined frequency. Ultrasonic blade 452 extends along longitudinal axis 476 coupled to transducer 14, and has body 454 having proximal end 456 and distal end 458. Distal end 458 is moveable along longitudinal axis 476 by the vibrations produced by the transducer. Ultrasonic surgical instrument 450 further comprises non-vibrating clamp arm assembly 460 having proximal end 462 and distal end 464. Clamp arm assembly 460 further comprises proximal tissue pad segment 466, distal tissue pad segment 470, and tissue pad insert segment 468 positioned between proximal tissue pad segment 466 and distal tissue pad segment 470. Clamp arm assembly 460 is pivotally moveable from an open position as indicated in FIGS. 13-17 to a closed position as indicated in FIG. 18. Clamp arm assembly 460 pivots along arc 480 (FIGS. 17-18) such that when in a closed position, insert segment 468 may be positioned at a location corresponding to node 474.

FIG. 15 is a partial side view of one embodiment of ultrasonic surgical instrument 450 having raised insert segment 468 positioned in the tissue pad of clamp arm assembly 460. Raised tissue pad insert segment 468 results in increased frictional interference when clamp arm assembly 460 is in a closed position as indicated in FIG. 18. The increased frictional interference results in increased heat generation when clamp arm assembly 460 is in a closed position.

FIG. 16 is a partial side view of one embodiment of ultrasonic surgical instrument 450 having insert segment 468 positioned in the tissue pad of clamp arm assembly 460. Tissue pad insert segment 468 is positioned in the tissue pad such that when clamp arm assembly 460 is in a closed position (FIG. 18), the insert segment is offset a predetermined distance from node 474.

The various embodiments of ultrasonic surgical blade 452 illustrated in FIGS. 14-18 may have an exposed length ranging from approximately one quarter of a wavelength (λ/4) of the ultrasonic vibrational wave to approximately one full wavelength (λ) of the ultrasonic vibrational wave. In various embodiments, the length of ultrasonic surgical blade 452 is approximately three quarters of a wavelength (3λ/4) of the ultrasonic vibrational wave. For example, the length of a curved titanium blade operating at a frequency of 55.5 kHz is approximately three quarters of a wavelength (3λ/4) of the ultrasonic vibrational wave or approximately 49 mm. Those of ordinary skill in the art will recognize that the location of node 474 (and consequently the nodal gap) will determine the positioning and location of the various components comprising ultrasonic surgical instrument 450.

Those of ordinary skill in the art will recognize that tissue pad insert segment 468 may be dimensioned and positioned in the tissue pad of clamp arm assembly 460 in order to achieve the desired frictional heating effects. For example, in various embodiments, tissue pad insert segment 468 may be raised relative to the nominal height of the tissue pad (comprising proximal tissue pad segment 466 and distal tissue pad segment 470) and may be offset from node 474 when clamp arm assembly 460 is in a closed position. In various embodiments, tissue pad insert segment 468 may be flush with the top surface of the tissue pad and centered on node 474. In other embodiments, tissue pad insert segment 468 may be raised relative to the nominal height of the tissue pad and centered on node 474. In still other embodiments, tissue pad insert segment 468 may be flush with the top surface of the tissue pad and may be offset from node 474. Tissue pad insert segment 468 can be dimensioned (i.e., have length, width and thickness) in order to achieve desired fractional heating effects. The flexibility in the positioning and dimensioning of tissue pad insert segment 468 allows the profile of the additional heat frictionally-generated along blade 452 to be designed for a given application.

Tissue pad insert segment 468 can be manufactured from any material suitable for frictionally-generating heat when forced against ultrasonic surgical blade 452. Exemplary materials for tissue pad insert segment 468 include polymeric materials with high melting temperatures and high effective coefficients of friction. Polyimide is one such exemplary material. Furthermore, tissue pad insert segment 468 may be a raised region of the tissue pad where insert segment 468, proximal tissue pad segment 466 and distal tissue pad segment 470 are all the same material and manufactured as one continuous component in a single unit of construction.

FIG. 19 is a partial side view of one embodiment of multiple-element end effector 600 comprising clamp arm assembly 602 and surgical blade 604. Clamp arm assembly 602 is shown in an open position and comprises clamp arm 603, proximal tissue pad segment 606, tissue pad insert segment 608 and distal tissue pad segment 610. Insert segment 608 may be positioned between proximal tissue pad segment 606 and distal tissue pad segment 610 on clamp arm 603 at a location that corresponds to nodal gap region 614 of blade 604 when clamp arm assembly 602 is in a closed position. In one embodiment, insert segment 608 may be located at or near node 612 and positioned within nodal gap 614 when clamp arm assembly 602 is in a closed position. In another embodiment, insert segment 608 may be located within nodal gap 614 but offset from node 612 (not shown). In yet another embodiment, the length of insert segment 608 along clamp arm 603 may correspond to the length of nodal gap 614 (not shown). In still another embodiment, insert segment 608 may be offset from node 612 and completely or partially outside nodal gap 614 (not shown). FIG. 20 is a perspective view of one embodiment of multiple-element end effector 600 of FIG. 19.

FIG. 21 is a partial side view of one embodiment of multiple-element end effector 650 comprising clamp arm assembly 652 and surgical blade 654. Clamp arm assembly 652 is shown in an open position and comprises clamp arm 653, proximal tissue pad segment 656, tissue pad insert segment 658 and distal tissue pad segment 660. Clamp arm assembly 652 further comprises biasing means 665. Biasing means 665 comprises a mechanism that provides additional force that forces insert segment 658 against blade 654 with greater force than the surrounding tissue pad (i.e., biasing means 665 force insert segment 658 against blade 654 with greater force than is exerted against blade 654 by proximal tissue pad segment 656 and distal tissue pad segment 660 when clamp arm assembly 652 is in a closed position). Biasing means 665 may comprise a leaf spring or other mechanism that is capable of providing increased force to blade 654 through insert segment 658.

Insert segment 658 may be positioned between proximal tissue pad segment 656 and distal tissue pad segment 660 on clamp arm 653 at a location that corresponds to a nodal gap region of blade 654 when clamp arm assembly 652 is in a closed position. In one embodiment, insert segment 658 may be located at or near node 662 and positioned within the nodal gap when clamp arm assembly 652 is in a closed position. In another embodiment, insert segment 658 may be located within the nodal gap but offset from node 662 (not shown). In yet another embodiment, the length of insert segment 658 along clamp arm 653 may correspond to the length of the nodal gap (not shown). In still another embodiment, insert segment 658 may be offset from node 662 and completely or partially outside the nodal gap (not shown).

FIGS. 13-21 illustrate various embodiments comprising blades and clamp arm assemblies comprising proximal tissue pad segments, distal tissue pad segments and tissue pad insert segments. The pivotal movement of the clamp arm assemblies with respect to the blades may be affected by the provision of a pair of pivot points on the clamp arm portion of the clamp arm assembly that interfaces with an ultrasonic surgical instrument via weld pin fastening or other fastening means (not shown). The tissue pad segments may be attached to the clamp arm by mechanical means including, for example, rivets, glues, adhesives, epoxies, press fitting or any other fastening means known in the art. Furthermore, the tissue pad segments may be removably attached to the clamp arm by any known means.

In various embodiments, the clamp arm may comprise a T-shaped slot for accepting a T-shaped flange of a proximal tissue pad segment, a distal tissue pad segment and a tissue pad insert segment. In various embodiments, a single unitary tissue pad assembly may comprise the proximal tissue pad segment, the distal tissue pad segment and the tissue pad insert segment, and further comprise a T-shaped flange for reception in a T-shaped slot in the clamp arm assembly. Additional configurations including dove tailed-shaped slots and wedge-shaped flanges are contemplated. As would be appreciated by those skilled in the art, flanges and corresponding slots have alternative shapes and sizes to removably secure the tissue pad segments to the clamp arm.

A method for replacing the proximal tissue pad segment, the distal tissue pad segment and/or the tissue pad insert segment include one or more of the steps of: a) disengaging the clamp arm assembly from the ultrasonic surgical instrument; b) removing at least one of the tissue pad segments from the clamp arm; c) inserting at least one new or reconditioned tissue pad segment into the clamp arm; and d) engaging the clamp arm assembly with the ultrasonic surgical instrument. In this removal and replacement process, the new or reconditioned proximal tissue pad segment, distal tissue pad segment and tissue pad insert segment may be multiple separate segments or of unitary construction.

Another method for replacing the proximal tissue pad segment, the distal tissue pad segment and/or the tissue pad insert segment include one or more of the steps of: a) opening flanges on the clamp arm; b) removing at least one of the tissue pad segments from the clamp arm; c) inserting at least one new or reconditioned tissue pad segment into the clamp arm; and d) closing flanges on the clamp arm. In this removal and replacement process, the new or reconditioned proximal tissue pad segment, distal tissue pad segment and tissue pad insert segment may be multiple separate segments or of unitary construction.

FIGS. 22-25 illustrate various embodiments of an ultrasonic surgical instrument comprising a pad for generating frictional heat when engaged with an operating ultrasonic surgical blade. FIG. 22A is a partial side view of one embodiment of ultrasonic surgical instrument 500 in an open position and inactive and having pad 522 positioned toward distal end 528 of extension member 520. FIG. 22B is an end view of one embodiment of the ultrasonic surgical instrument of FIG. 22A. Pad 522 is disposed adjacent to blade body 504. Pad 522 is positioned on extension member 520 toward distal end 528 and located between blade body 504 and distal end 528 of extension member 520. Ultrasonic surgical instrument 500 comprises outer tube 518. Ultrasonic surgical blade 502 extends along longitudinal axis 524 coupled to transducer 14 (FIG. 1), and has body 504 having proximal end 506 and distal end 508. Distal end 508 is moveable along longitudinal axis 524 by the vibrations produced by transducer 14. Ultrasonic surgical instrument 500 further comprises non-vibrating clamp arm assembly 510 having proximal end 512 and distal end 514. Clamp arm assembly 510 further comprises tissue pad 516.

Ultrasonic surgical blade 502 is positioned such that a length equal to approximately three-quarters ($3\lambda/4$) of a wavelength of the ultrasonic vibrational wave is exposed. Clamp arm assembly 510 is pivotally moveable from an open position to a closed position. Clamp arm assembly 510 may pivot along an arc in a manner analogous to clamp arm 460 discussed in conjunction with FIGS. 17 and 18. In various embodiments, extension member 520 may be an extension of outer tube 518 (i.e., an outer tube member). Extension member 520 may be curved in a manner similar to the curvature of outer tube 518 perpendicular to longitudinal axis 524 (FIGS. 22B, 23B and 24B). The curvature of extension member 520 may impart substantially greater flexural stiffness to extension member 520 compared to a flat construction. The increased flexural stiffness of extension member 520 is advantageous because it resists deflection of extension member 520 when blade 502 engages pad 522.

In other embodiments, extension member 520 may be a component separate from outer tube 518. For example, extension member 520 may be a protective sheath comprising proximal end 526 and distal end 528 and disposed adjacent to blade body 504. Pad 522 may be positioned on protective sheath 520 toward distal end 528 and located between body 504 and distal end 528 of protective sheath 520. In various embodiments, protective sheath 520 may be fixedly attached to ultrasonic surgical instrument 500. In other embodiments, protective sheath 520 may be slideably engaged with ultrasonic surgical instrument 500. In various embodiments, protective sheath 520 may be deployable by advancing protective sheath 520 along longitudinal axis 524 toward distal end 508 of blade 502. Protective sheath 520 may be retractable toward a proximal end along longitudinal axis 524.

FIG. 23A is a partial side view of one embodiment of ultrasonic surgical instrument 500 in a closed position and activated, where pad 522 is engaged with blade body 504 at interface 530. FIG. 23B is an end view of one embodiment of the ultrasonic surgical instrument of FIG. 23A. In the closed position, clamp arm 510 engages body 504 of blade 502 on bottom surface 528. A biasing force provided by clamp arm assembly 510 causes blade 502 to deflect toward extension member 520. Blade 502 deflects and contacts pad 522 at top surface 526 of blade body 504. Pad 522 and blade body 504 engage at interface 530. The frictional interaction between pad 522 and activated blade body 504 at interface 530 generates heat that conducts into blade 502. The conducted heat may produce cutting and/or coagulation temperatures in the region of blade 502 engaged with pad 522. If pad 522 is positioned such that interface 530 is located at or near a node (not shown), then the frictionally-generated heat will fill the nodal energy gap, effectively extending the active length of blade 502 from approximately one-quarter of a vibrational wavelength (λ/4) to approximately three-quarters of a vibrational wavelength (3λ/4) (e.g., approximately 49 mm for a curved titanium blade operating at 55.5 kHz).

FIG. 24A is a partial side view of one embodiment of ultrasonic surgical instrument 500 in an open position and activated, where pad 522 is not engaged with blade body 504 and no heat is frictionally-generated by pad 522. FIG. 24B is an end view of one embodiment of the ultrasonic surgical instrument of FIG. 24A. This configuration may be a back-cutting mode, for example, where the standard active length (one quarter of a vibrational wavelength (λ/4)) is available for back-cutting and/or coagulation where tissue is not forced against blade body 504 by clamp arm assembly 510.

FIG. 25A is a partial side view of one embodiment of ultrasonic surgical instrument 500 in an open position and inactive, where pad 522 is positioned on extension member 520 located at node 532. In a closed position (not shown), pad 522 will engage blade body 504 in the nodal gap and centered on node 532. FIG. 25B is a partial side view of one embodiment of ultrasonic surgical instrument 500 in an open position and inactive where pad 522 is positioned on extension member 520 offset distally from node 532. FIG. 25C is a partial side view of one embodiment of ultrasonic surgical instrument 500 in an open position and inactive where pad 522 is positioned on extension member 520 offset proximally from node 532. FIG. 25D is a partial side view of one embodiment of ultrasonic surgical instrument 500 in an open position and inactive where pad 522 is positioned on extension member 520 spanning node 532 and having a different length than pad 522 as illustrated in the embodiments of FIGS. 25A-C. Those of ordinary skill will recognize that the length, width, thickness and offset of pad 522 relative to node 532 can be varied to achieve predetermined effects. For example, the flexibility in the positioning and dimensioning of pad 522 allows the profile of the additional heat frictionally-generated along blade 502 to be designed for a given application.

Pad 522 can be manufactured from any known material suitable for frictionally-generating heat when forced against ultrasonic surgical blade 502. Exemplary materials for pad 522 include polymeric materials with high melting temperatures and high effective coefficients of friction. Polyimide is one such exemplary material. Furthermore, pad 522 may be a raised region of extension member 520. In various embodiments, extension member 520 and pad 522 may be manufactured as a continuous component of the same material in a single unit of construction.

Additional advantages of pad 522 include that pad 522 provides mechanical support to ultrasonic surgical blade 502 having increases exposed length. In this regard, pad 522 functions in a dual role; generating heat to fill the nodal energy gap and supporting the increased mechanical load on deflected blade 502 when engaged with activated blade body 504 when clamp arm assembly 510 is in a closed position (see FIGS. 23A and 23B).

FIGS. 26A-E illustrate various embodiments of single-element end effectors. FIGS. 26A-C are cross-sectional side views of single-element end effector 550 comprising internal cavity 570 positioned in region 560. FIGS. 26D-E are cross-sectional end views of single-element end effector 550 comprising internal cavity 570. Internal cavity 570 effectively reduces the cross-sectional area, and therefore, the specific acoustic impedance value, of end effector 550 in region 560. The specific acoustic impedance value may change abruptly (FIG. 26A) or gradually (FIG. 26B-C) along the length of end effector 550. The present invention is not limited to any particular geometry in the context of internal cavity 570 as illustrated in FIGS. 26A-E, showing internal cavity 570 comprising different non-limiting geometries. In various embodiments, end effector 550 may comprise a single unit of construction comprising a single material having internal cavity 570 formed therein. In various embodiments, end effector 550 may comprise a plurality of discontinuous internal cavities 570 (not shown). In various embodiments, end effector 550 may comprise one or more holes along an axis of end effector 550 that are open to an external surface of end effector 550 and that create reductions in the cross sectional area of end effector 550.

In various embodiments, an end effector may comprise a single unit of solid construction comprising a single material and having no cavities, where the specific acoustic impedance of the end effector changes along its length, either gradually or abruptly. In such embodiments, the desired specific acoustic impedance profile along the length of the end effector can be formed by cold working the end effector.

In various embodiments, the methods and techniques for bridging and filling the nodal gap are combined in ultrasonic surgical instruments. For example, in various embodiments an ultrasonic surgical instrument may have both a tissue pad insert segment positioned on a clamp arm assembly and a pad positioned on an extension member. In other embodiments, an ultrasonic surgical instrument may have a tissue pad insert segment on a clamp arm assembly and an end effector having an insert segment having a relatively low specific acoustic impedance value and/or comprising a lossy material or a high friction material (or coatings of such materials on the end effector). In still other embodiments, an ultrasonic surgical instrument may have a pad positioned on an extension member and an end effector having an insert segment having a relatively low specific acoustic impedance value and/or comprising a lossy material or high friction material (or coatings of such materials on the end effector). It is also contemplated that an ultrasonic surgical instrument may have a tissue pad insert segment positioned on a clamp arm assembly, a pad positioned on an extension member, and an end effector having an insert segment having a relatively low specific acoustic impedance value and/or comprising a lossy material or high friction material (or coatings of such materials on the end effector) (FIG. 27). The present invention is not limited in this context and various combinations and/or modifications to the described configurations for ultrasonic surgical instruments are contemplated.

FIG. 27 is a partial side view of one embodiment of ultrasonic end effector 700 having insert segment 710 positioned in blade 716, tissue pad insert segment 720 positioned in the tissue pad 724 of clamp arm assembly 726 and pad 730 positioned on extension member 736.

The devices disclosed herein can be designed to be disposed of after a single use, or they can be designed to be used multiple times. In either case, however, the devices can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a transducer configured to produce vibrations along a longitudinal axis at a predetermined frequency;
   an ultrasonic blade extending along the longitudinal axis coupled to the transducer, wherein the ultrasonic blade comprises a body having a proximal end and a distal end, wherein the distal end is movable along the longitudinal axis by the vibrations produced by the transducer; and
   a non-vibrating clamp arm assembly having a proximal end and a distal end and pivotally positioned adjacent to the body, wherein the clamp arm assembly is pivotally movable from an open position to a closed position, wherein the clamp arm assembly comprises a proximal tissue pad segment, a distal tissue pad segment, and a tissue pad insert segment positioned between the proximal tissue pad segment and the distal tissue pad segment;
   wherein the tissue pad insert segment is raised relative to a nominal height of the proximal tissue pad segment and the distal tissue pad segment.

2. The surgical instrument of claim 1, wherein the tissue pad insert segment is positioned at a location corresponding to a nodal gap region when the clamp arm assembly is in the closed position.

3. The surgical instrument of claim 1, wherein the tissue pad insert segment is positioned at a location offset from a nodal gap when the clamp arm assembly is in the closed position.

4. The surgical instrument of claim 1, wherein the tissue pad insert segment comprises polyimide.

5. The surgical instrument of claim 1, wherein the proximal tissue pad segment and the distal tissue pad segment comprise polytetrafluoroethylene.

6. A surgical instrument, comprising:
   a transducer configured to produce vibrations along a longitudinal axis at a predetermined frequency;
   an ultrasonic blade extending along the longitudinal axis coupled to the transducer, wherein the ultrasonic blade comprises a body having a proximal end and a distal end, wherein the distal end is movable along the longitudinal axis by the vibrations produced by the transducer; and
   a non-vibrating clamp arm assembly having a proximal end and a distal end and pivotally positioned adjacent to the body, wherein the clamp arm assembly is pivotally movable from an open position to a closed position, wherein the clamp arm assembly comprises a proximal tissue pad segment, a distal tissue pad segment, and a tissue pad insert segment positioned between the proximal tissue pad segment and the distal tissue pad segment;
   wherein the clamp arm assembly further comprises biasing means configured to force the tissue pad insert segment against the ultrasonic blade with increased force relative to the proximal tissue pad segment and the distal tissue pad segment when the clamp arm assembly is in the closed position.

7. The surgical instrument of claim 6, wherein the tissue pad insert segment is positioned at a location corresponding to a nodal gap region when the clamp arm assembly is in the closed position.

8. The surgical instrument of claim 6, wherein the tissue pad insert segment is positioned at a location offset from a nodal gap when the clamp arm assembly is in the closed position.

9. The surgical instrument of claim 6, wherein the tissue pad insert segment comprises polyimide.

10. The surgical instrument of claim 6, wherein the proximal tissue pad segment and the distal tissue pad segment comprise polytetrafluoroethylene.

11. A surgical instrument, comprising:
    a transducer configured to produce vibrations along a longitudinal axis at a predetermined frequency;
    an ultrasonic blade extending along the longitudinal axis coupled to the transducer, wherein the ultrasonic blade comprises a body having a proximal end and a distal end, wherein the distal end is movable along the longitudinal axis by the vibrations produced by the transducer; and
    a non-vibrating clamp arm assembly having a proximal end and a distal end and pivotally positioned adjacent to the body, wherein the clamp arm assembly is pivotally movable from an open position to a closed position, wherein the clamp arm assembly comprises a proximal tissue pad segment, a distal tissue pad segment, and a tissue pad insert segment positioned between the proximal tissue pad segment and the distal tissue pad segment;
    wherein the clamp arm assembly further comprises a leaf spring configured to force the tissue pad insert segment against the ultrasonic blade with increased force relative to the proximal tissue pad segment and the distal tissue pad segment when the clamp arm assembly is in the closed position.

12. The surgical instrument of claim 11, wherein the tissue pad insert segment is positioned at a location corresponding to a nodal gap region when the clamp arm assembly is in the closed position.

13. The surgical instrument of claim 11, wherein the tissue pad insert segment is positioned at a location offset from a nodal gap when the clamp arm assembly is in the closed position.

14. The surgical instrument of claim 11, wherein the tissue pad insert segment comprises polyimide.

15. The surgical instrument of claim 11, wherein the proximal tissue pad segment and the distal tissue pad segment comprise polytetrafluoroethylene.

\* \* \* \* \*